United States Patent
Iorio et al.

(10) Patent No.: US 10,487,124 B2
(45) Date of Patent: Nov. 26, 2019

(54) LANTIPEPTIDE

(75) Inventors: Marianna Iorio, Milan (IT); Sonia Maffioli, Milan (IT); Paolo Monciardini, Milan (IT); Margherita Sosio, Milan (IT); Stefano Donadio, Milan (IT); Rosalia Bertorelli, Genoa (IT); Oscar Sasso, Genoa (IT); Angelo Reggiani, Genoa (IT)

(73) Assignees: NAICONS S.r.l., Milan (IT); FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 1027 days.

(21) Appl. No.: 14/414,446

(22) PCT Filed: Jul. 12, 2012

(86) PCT No.: PCT/IB2012/001373
§ 371 (c)(1),
(2), (4) Date: Jun. 1, 2015

(87) PCT Pub. No.: WO2014/009763
PCT Pub. Date: Jan. 16, 2014

(65) Prior Publication Data
US 2015/0291670 A1 Oct. 15, 2015

(51) Int. Cl.
C07K 14/365 (2006.01)
C12R 1/045 (2006.01)
A61K 38/00 (2006.01)

(52) U.S. Cl.
CPC .......... C07K 14/365 (2013.01); C12R 1/045 (2013.01); A61K 38/00 (2013.01)

(58) Field of Classification Search
None
See application file for complete search history.

(56) References Cited

U.S. PATENT DOCUMENTS

2012/0053115 A1   3/2012   Maffioli et al.

FOREIGN PATENT DOCUMENTS

WO   WO-2009121483 A1 * 10/2009   ............... C07K 7/08

OTHER PUBLICATIONS

*Actinoplanes* sp. DSM 24059 16S ribosomal RNA gene, partial sequence GenBank: KF438031.1, p. 1 (Year: 2013).*
*Actinoplanes* sp. NAI112 LantT (lanT), LabP (labP), LantT (lanT), ABC transporter permease, LabKC (labKC), LabA (labA), and Gtf (gtf) genes, complete cds, GenBank: KF765778.1, pp. 1-5 (Year: 2013).*
Monciardini et al., "Discovering new bioactive molecules from microbial sources", Microbial Biotechnoloy, 2014, pp. 209-220 (Year: 2014).*
AdipoGen, "NAI-112: Product Data Sheet", AdipoGen Life Sciences, 2018, p. 1 (Year: 2018).*
Iorio et al., A Glycosylated Labionin-Containing Lanthipeptide with Marked Antinociceptive Activity, ACS Chem. Biol., 2014, 398-404 (Year: 2014).*
Piper et al., Discovery of Medically Significant Lantibiotics Current Drug Discovery Technologies, 2009, 1-18 (Year: 2009).*
Meindl et al., Labyrinthopeptins: A New Class of Carbacyclic Lantibiotics, Angew Chem. Int. Ed, 2010, 1151-1154 (Year: 2010).*
Int'l Search Report for PCT/IB2012/001373, six pages, dated Mar. 27, 2013.
Written Opinion for PCT/IB2012/001373, four pages, dated Mar. 27, 2013.
Knerr et al. "Discovery, biosynthesis, and engineering of lantipeptides" *Annual Review of Biochemistry*, vol. 81, No. 1, pp. 479-505 (Jul. 2012).
Boakes et al. "Organization of the biosynthetic genes encoding deoxyactagardine B (DAB), a new lantibiotic produced by Actinoplanes liguriae NCIMB41362" *Journal of Antibiotics*, vol. 63, No. 7, pp. 351-358 (Jun 2010).
Int'l Preliminary Examination Report for PCT/IB2012/001373, six pages, dated Jan. 13, 2015.
Knerr & Van Der Donk "Discovery, biosynthesis, and engineering of lantipeptides" *Annual Review of Biochemistry*, vol. 81, No. 1, pp. 479-505 (Jul. 2012).

* cited by examiner

*Primary Examiner* — Lianko G Garyu
(74) *Attorney, Agent, or Firm* — Silvia Salvadori

(57) ABSTRACT

The present invention concerns novel lantipeptide (lanthionine-containing peptide) compounds having general formula (I), a process for their preparation, the key intermediates in said processes, their pharmaceutical acceptable salts and pharmaceutical compositions containing them, as well as their use in the treatment of pain.

18 Claims, 17 Drawing Sheets
Specification includes a Sequence Listing.

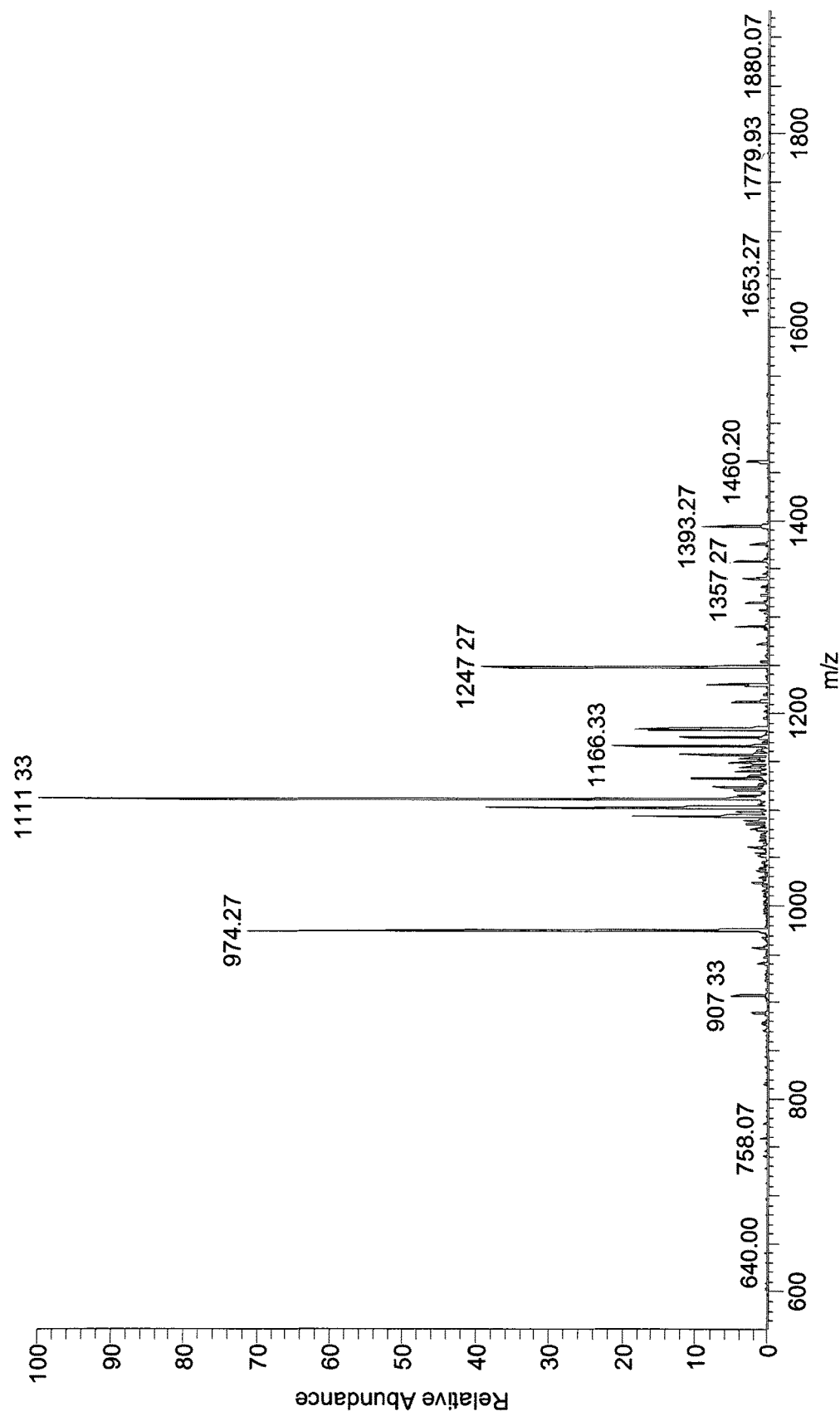
FIG 1A Fragmentation pattern of NAI-112a/b

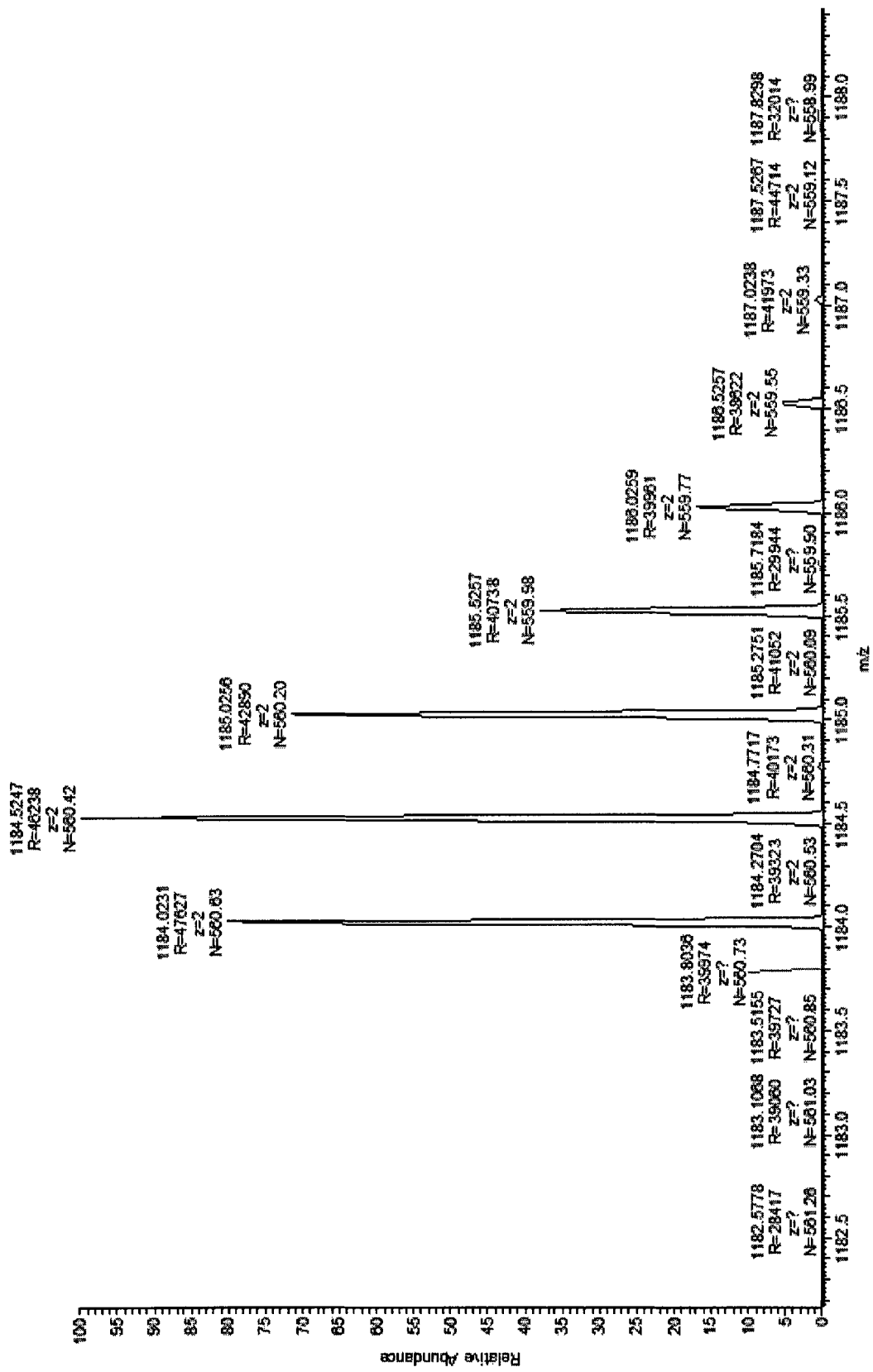
FIG 1B NAI-112a/b MS full-scan high resolution spectrum showing a doubly protonated ion at *m/z* 1184

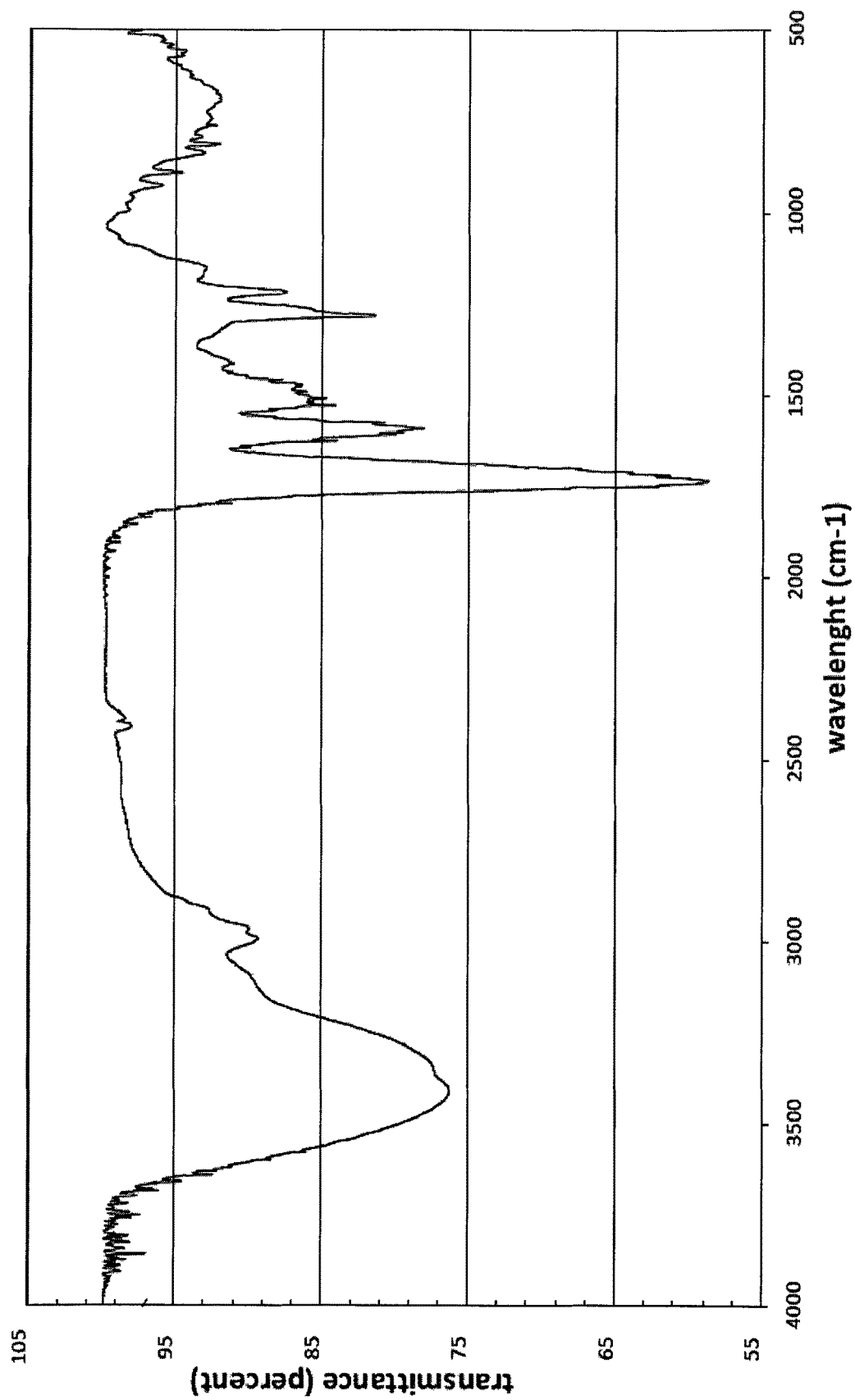
FIG.2 represents IR spectrum of NAI-112a/b in KBr

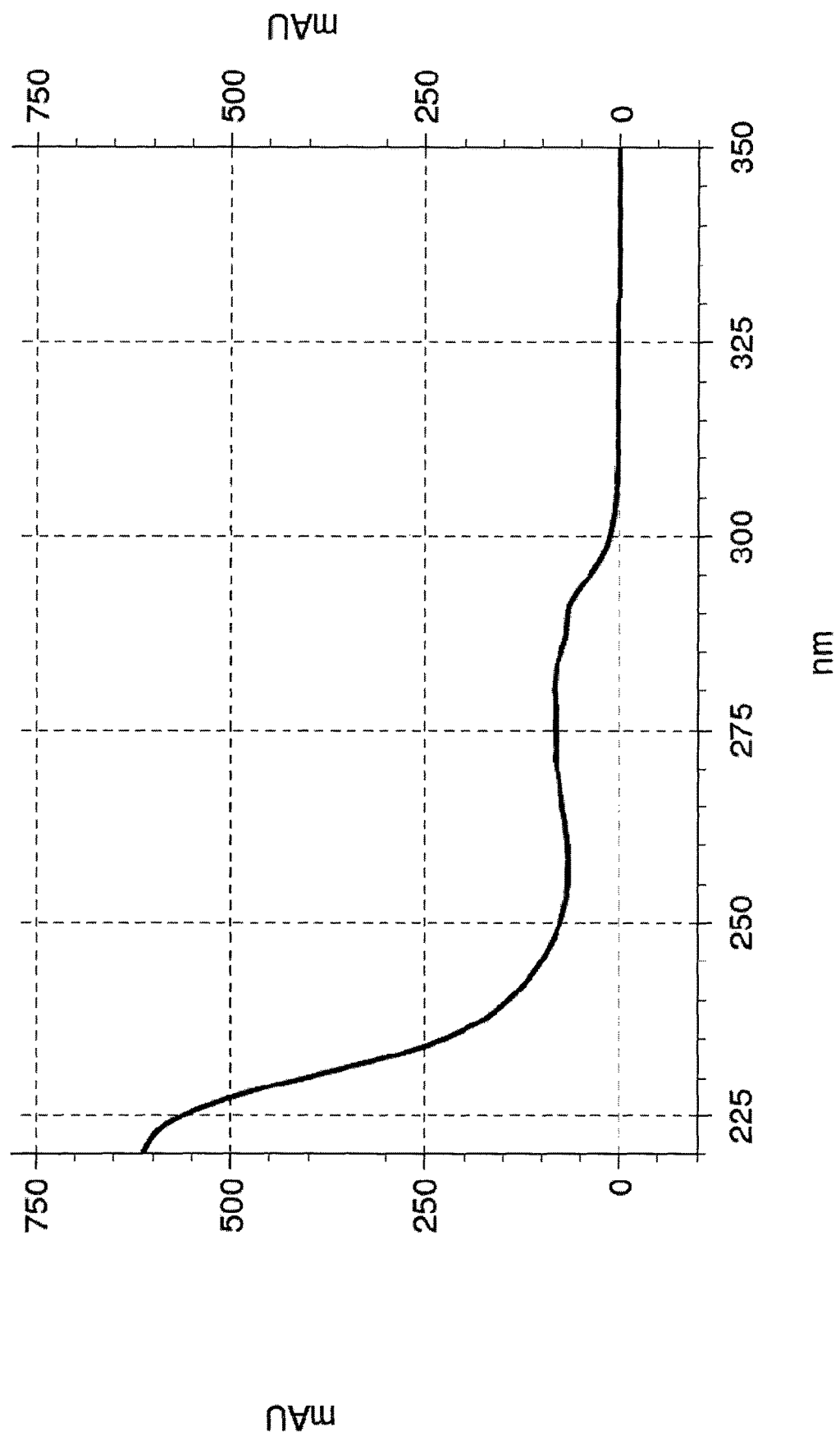
FIG 3 UV spectrum of antibiotic NAI-112a/b dissolved in Acetonitrile:water

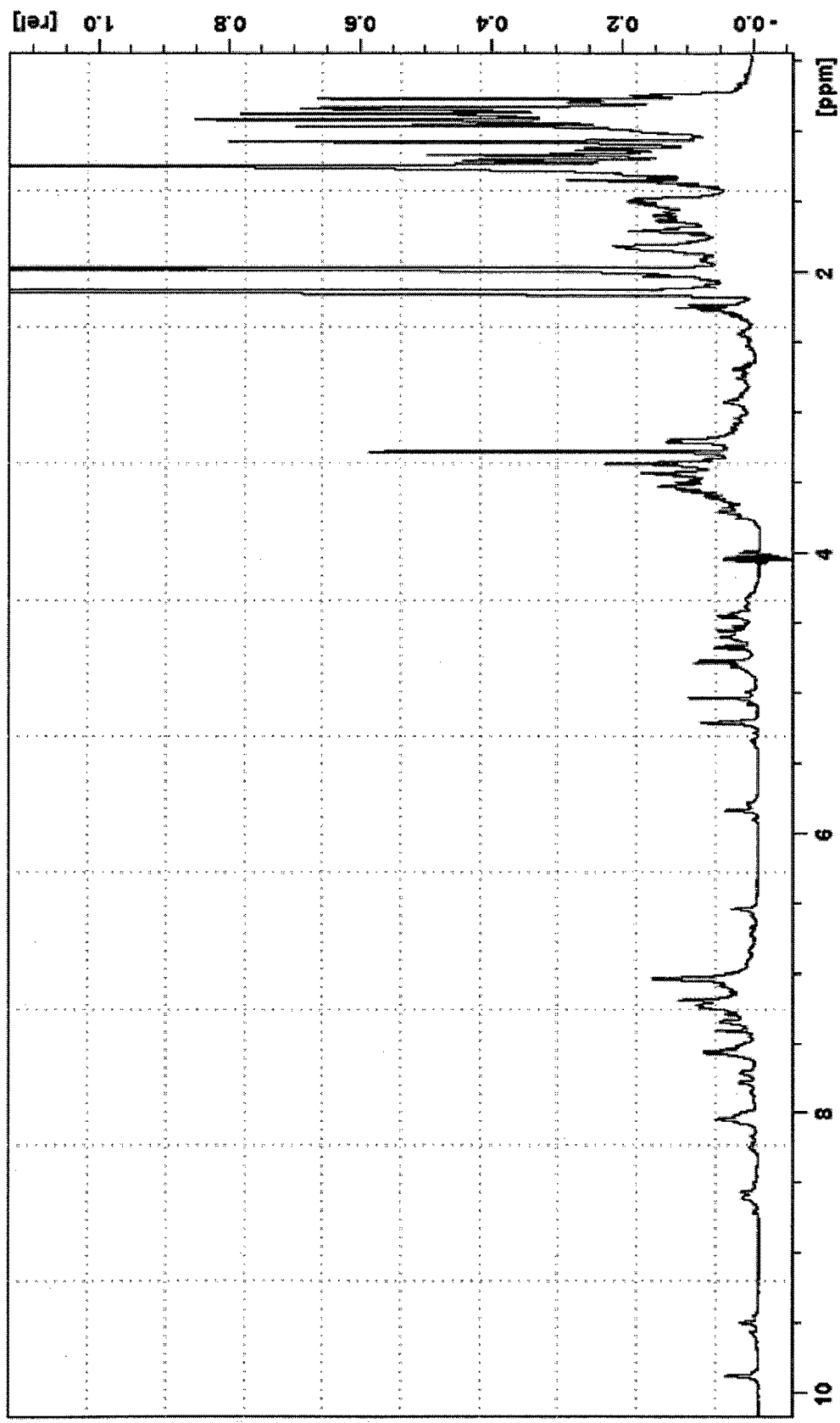
FIG. 4 $^1$H-NMR spectrum of NAI-112a/b recorded in the mixture Acetonitrile-d$_3$:D2O/H2O at 25°C on a Bruker AMX 600 spectrometer

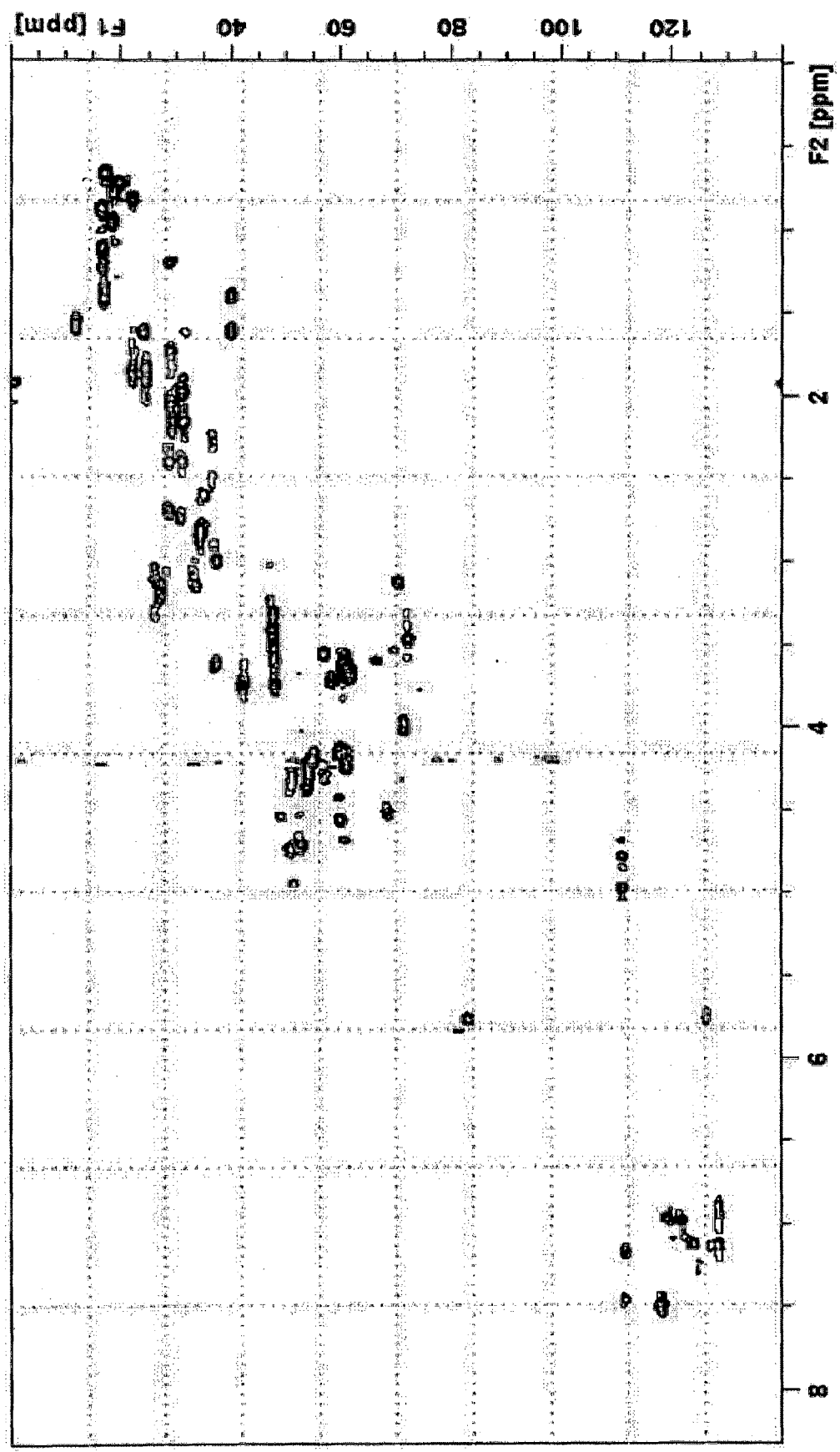
FIG 5 HSQC spectrum of NAI-112a/b recorded in the mixture Acetonitrile-d$_3$:D20 at 25°C on a Bruker AMX 600 spectrometer

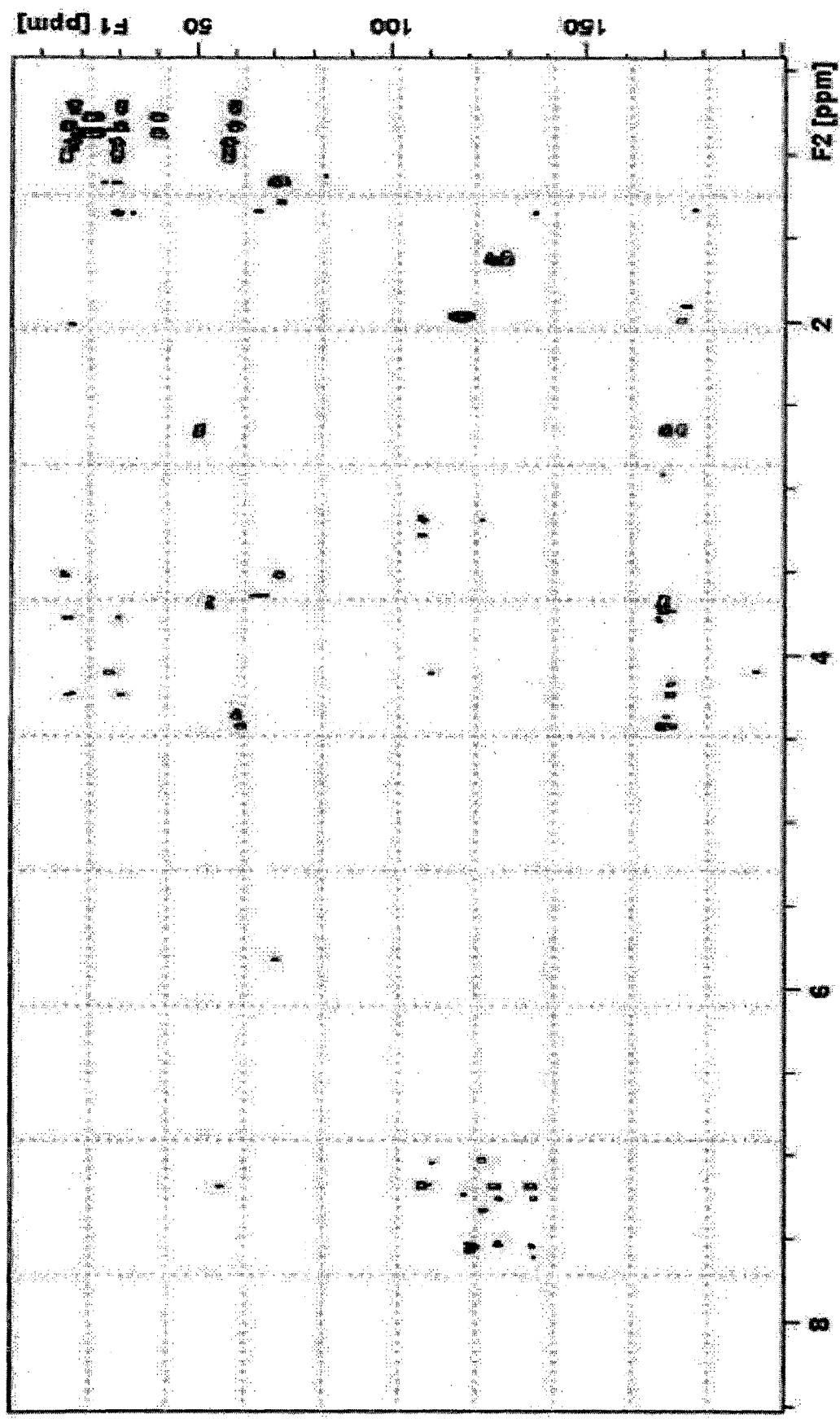
FIG 6 HMBC spectrum recorded in the mixture Acetonitrile-d₃,D2O at 25°C on a Bruker AMX 600 spectrometer

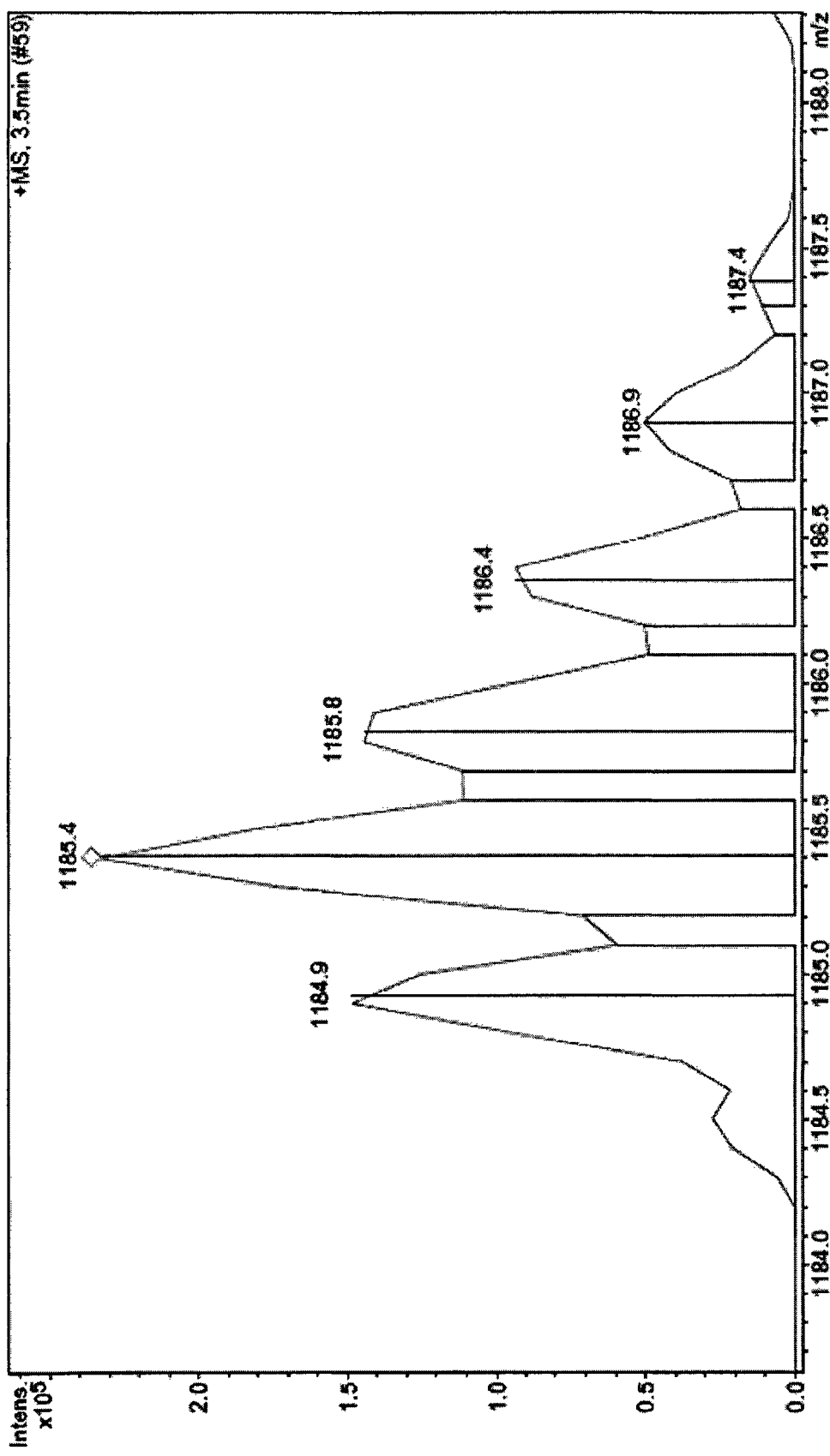
FIG. 7 NAI-112c/d full-scan low resolution spectrum showing a doubly protonated ion at m/z 1184.9.

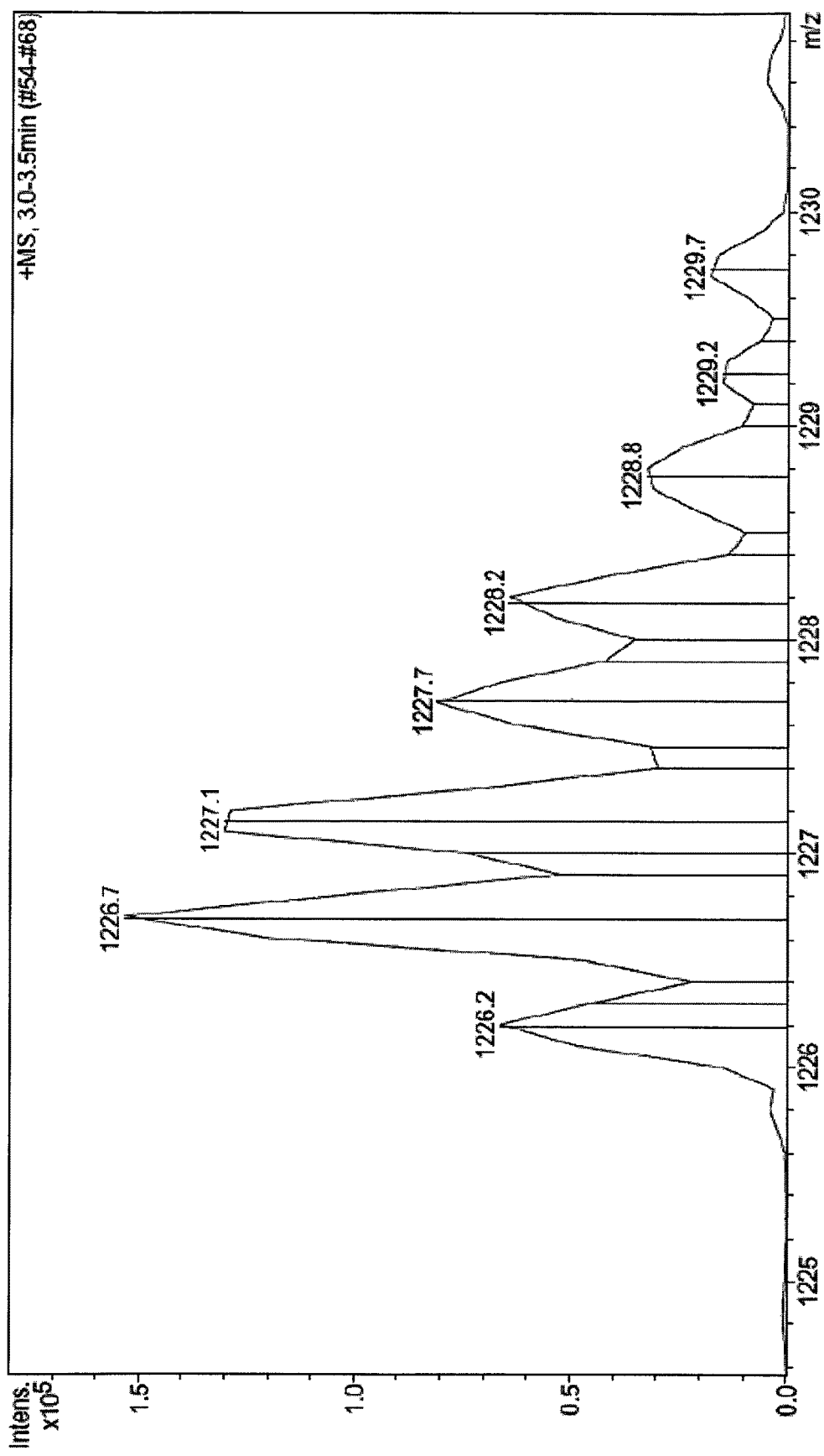
FIG. 8 NAI-112e/f full-scan low resolution spectrum showing a doubly protonated ion at *m/z* 1226.2.

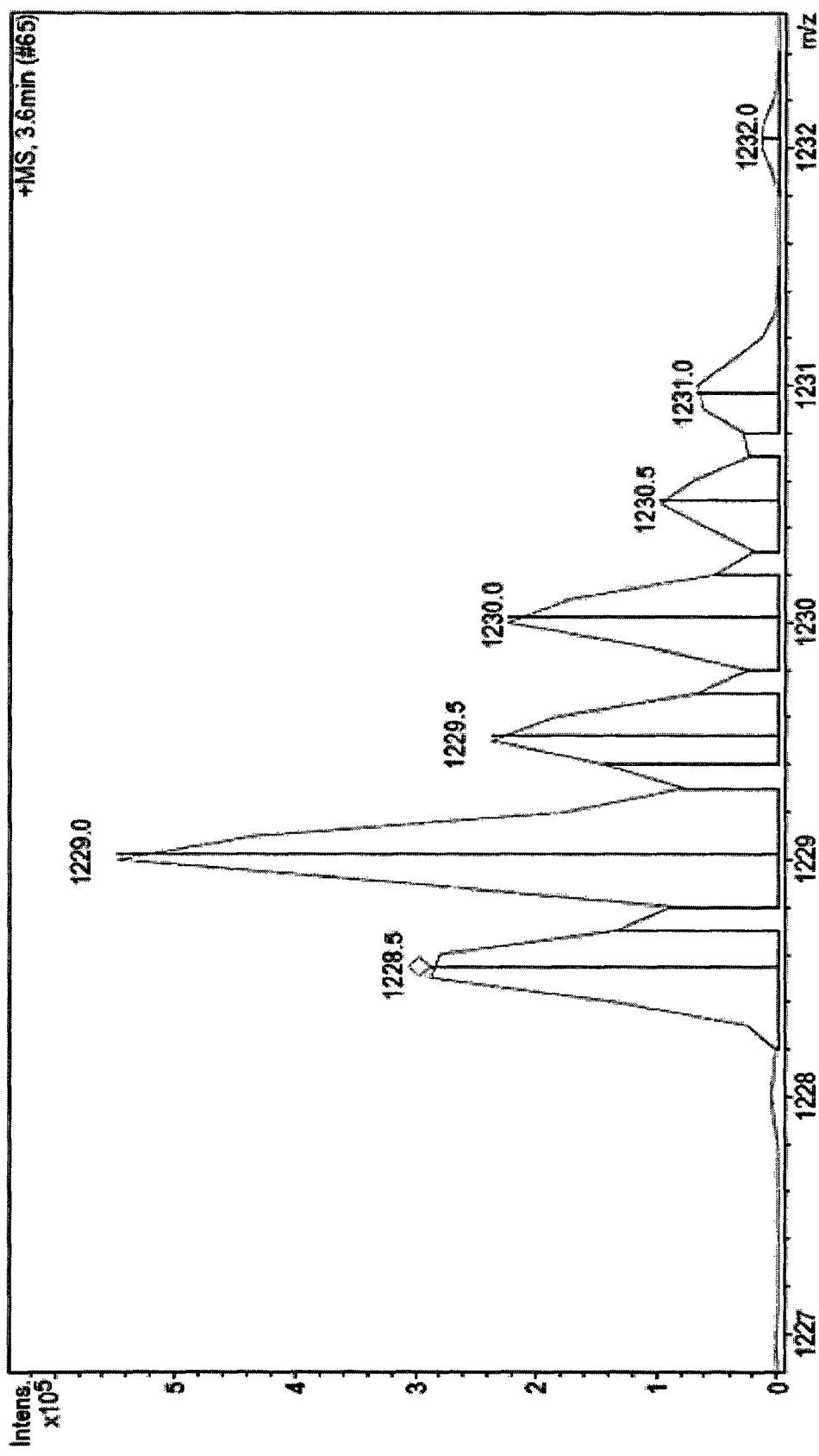
FIG 9 NAI-112g/h full-scan low resolution spectrum showing a doubly protonated ion at m/z 1228.5

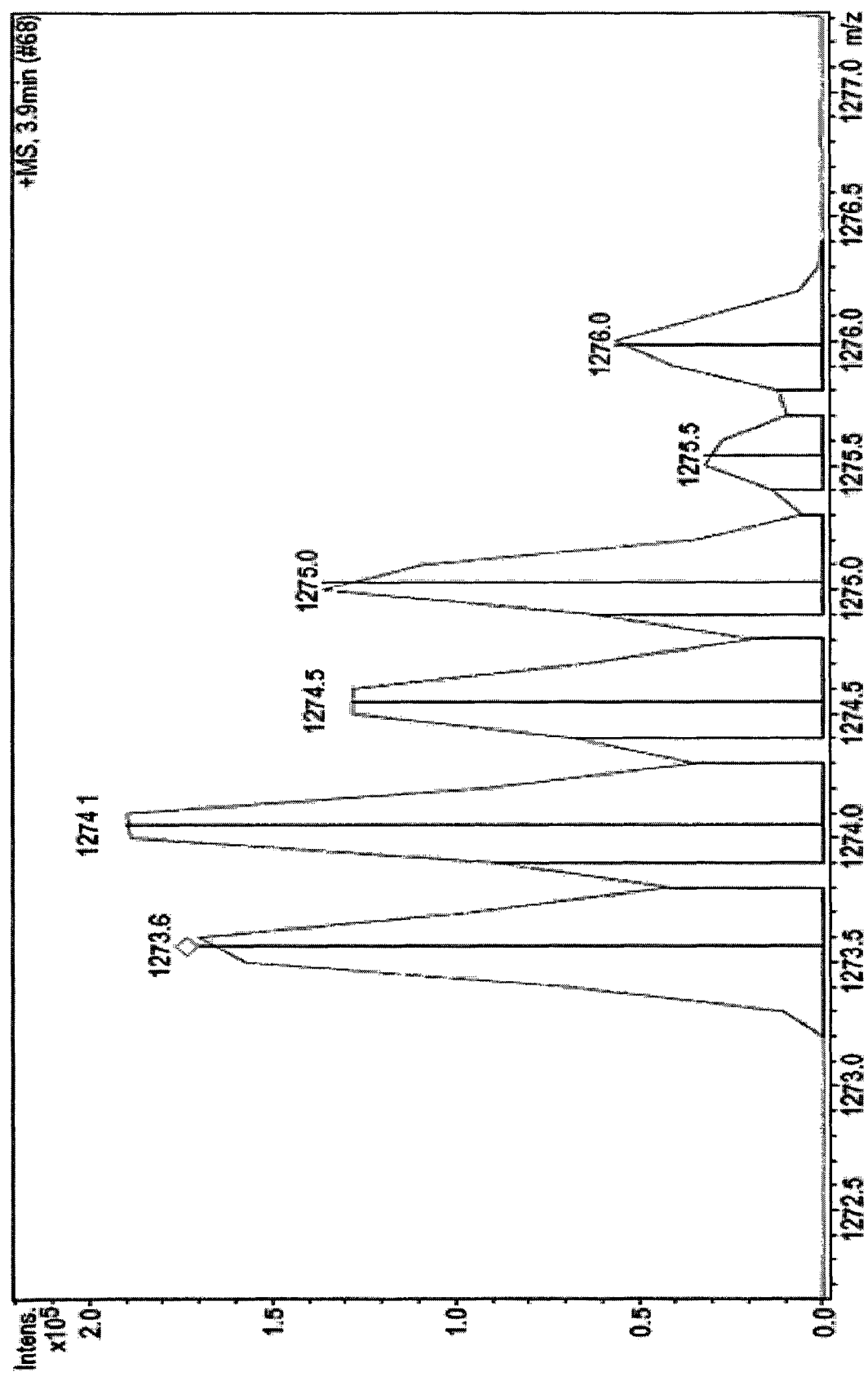
FIG.10 NAI-112i/l full-scan low resolution spectrum showing a doubly protonated ion at $m/z$ 1273.6.

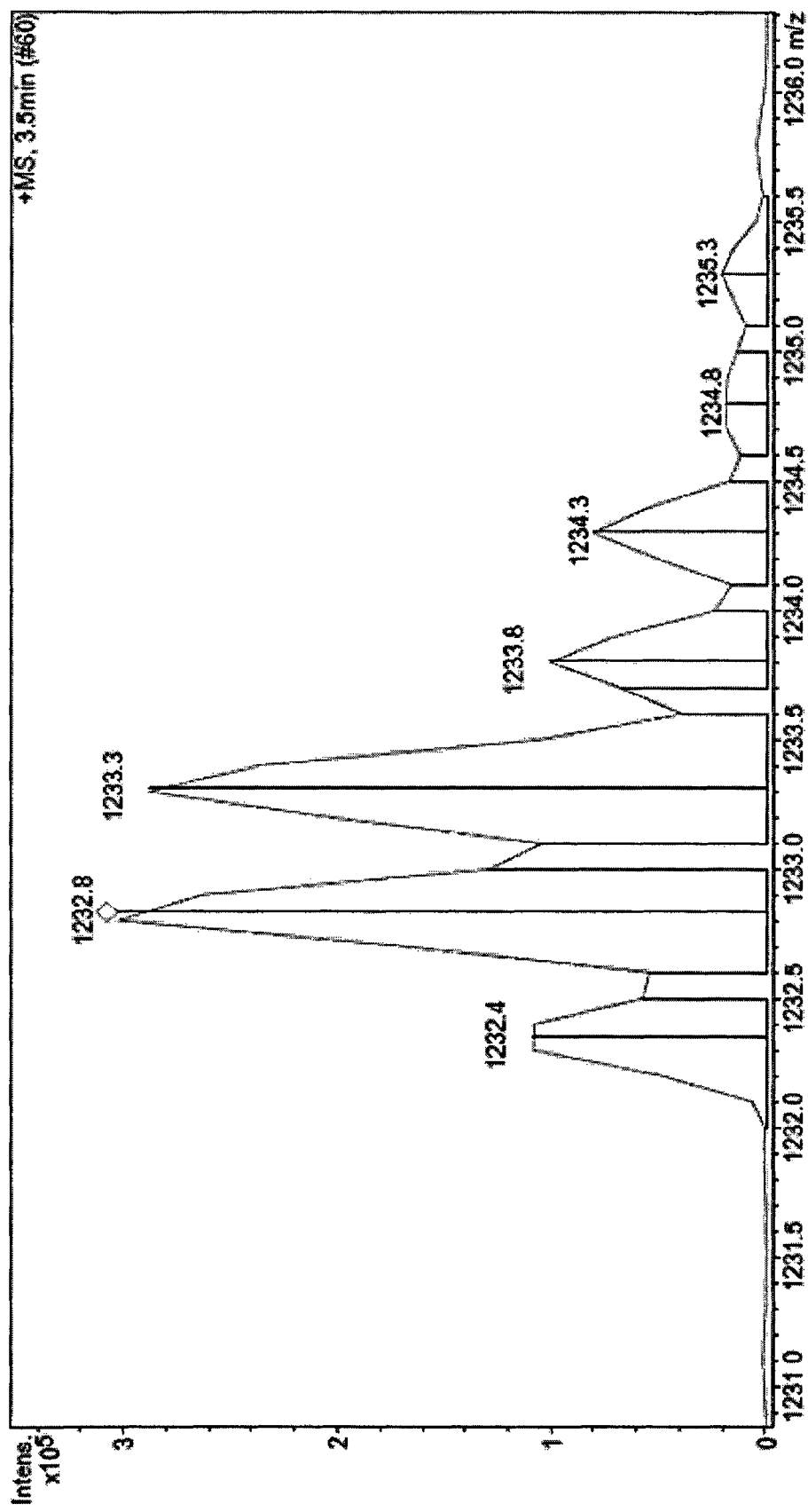
FIG 11 NAI-112 m/n full-scan low resolution spectrum showing a doubly protonated ion at m/z 1232.4

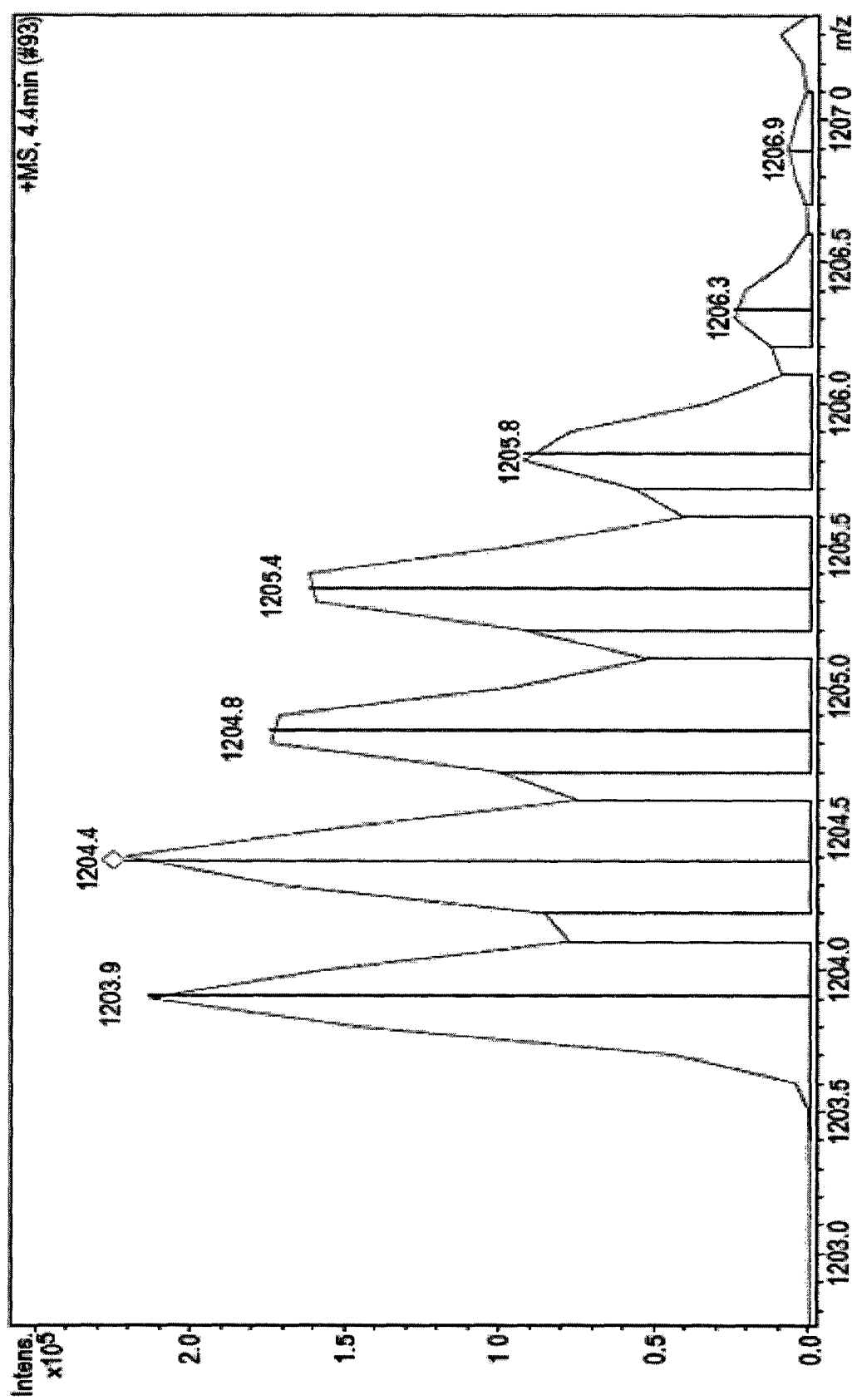
FIG 12 NAI-112o/p full-scan low resolution spectrum showing a doubly protonated ion at m/z 1203.9

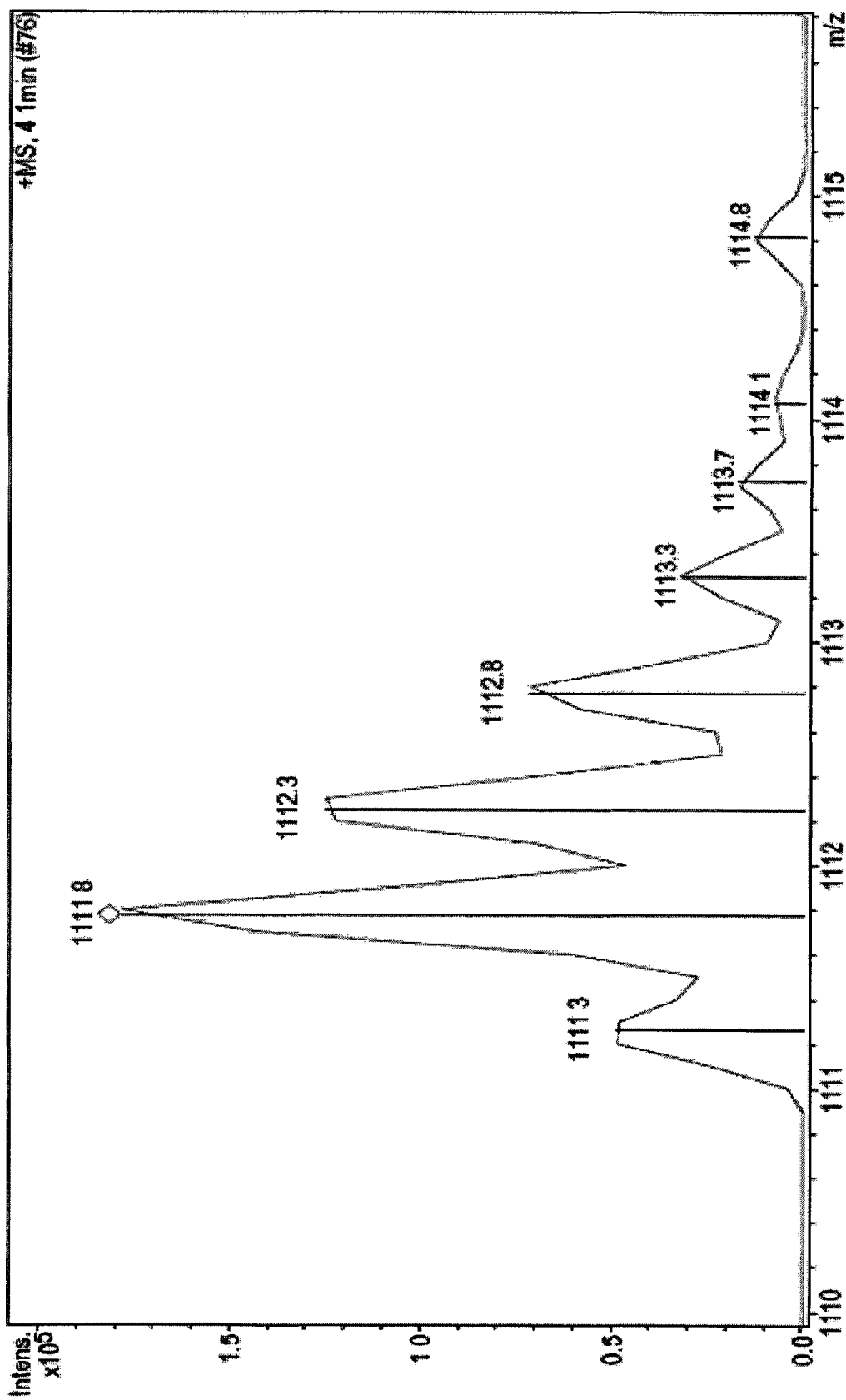
FIG 13 NAI-112q/r full-scan low resolution spectrum showing a doubly protonated ion at m/z 1111.3

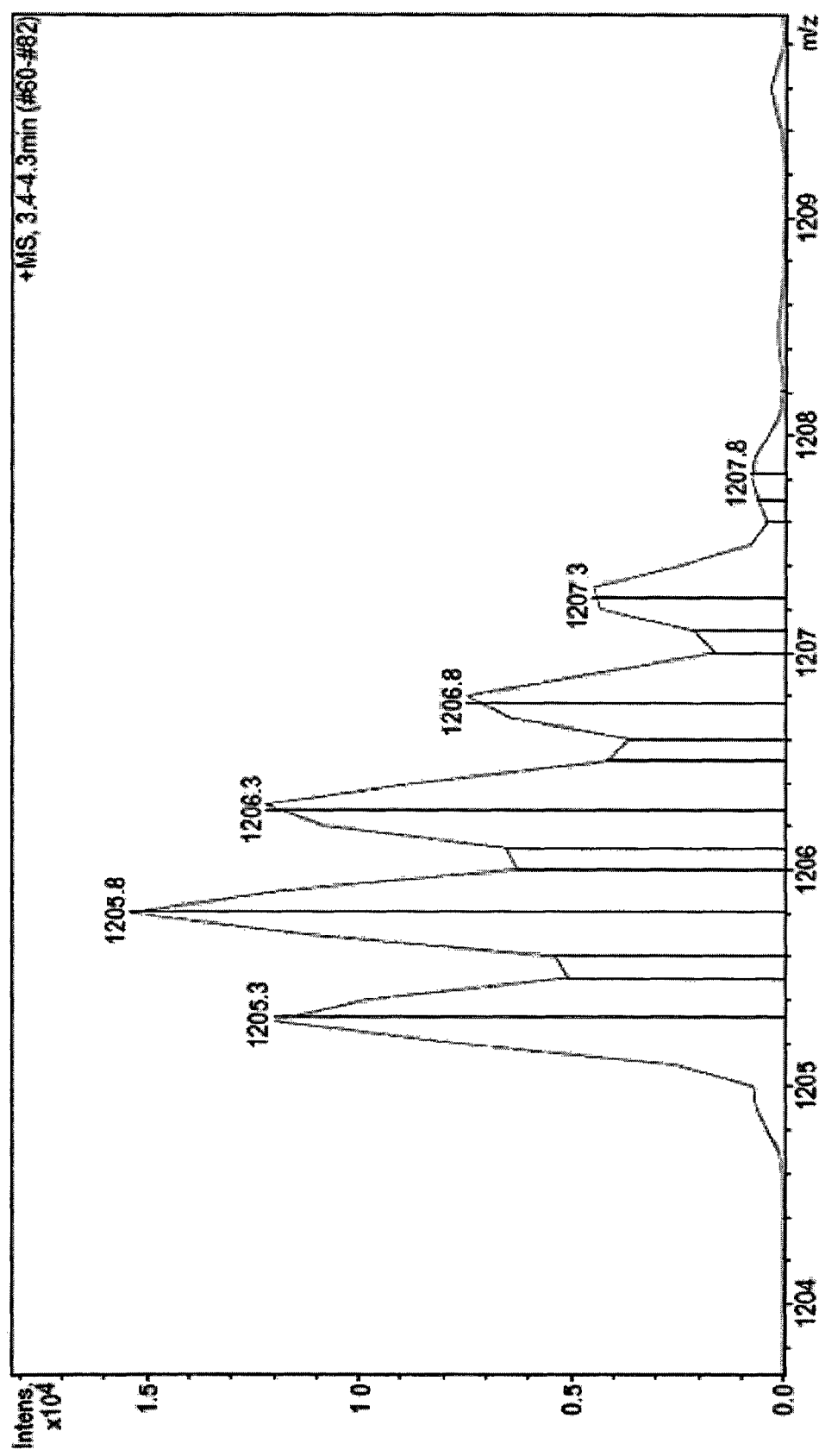
FIG 14 NAI-112s/t full-scan low resolution spectrum showing a doubly protonated ion at m/z 1205 3

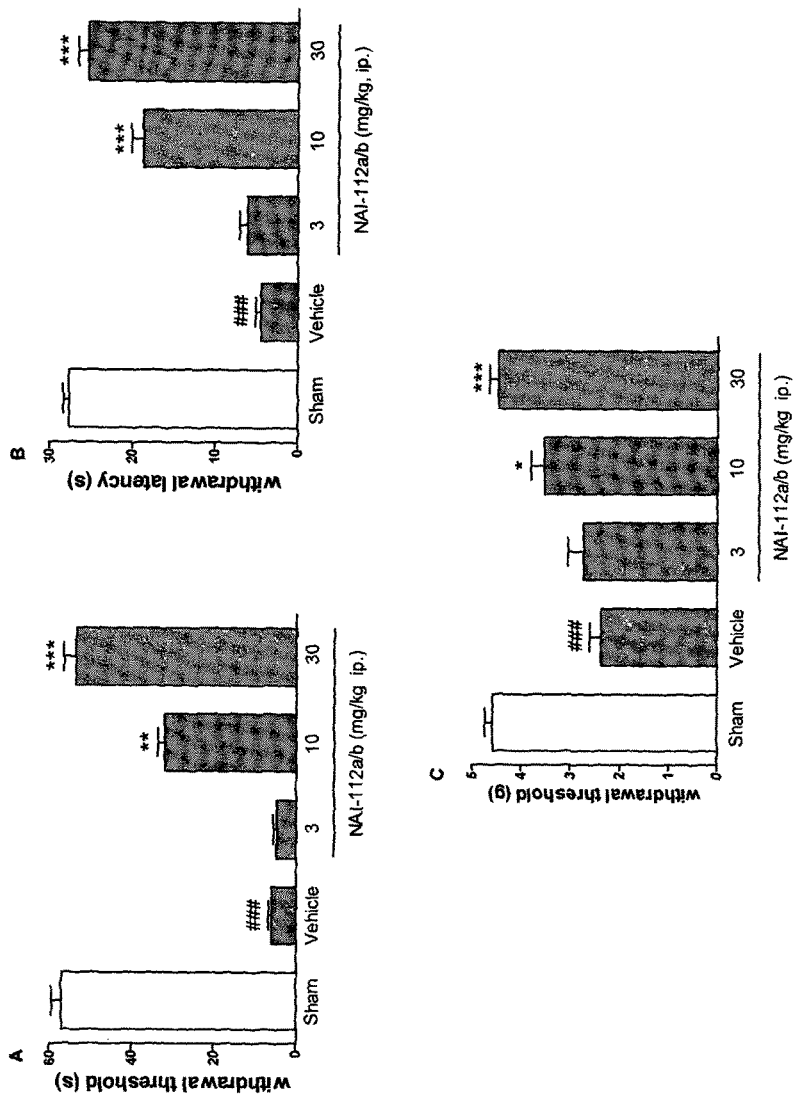
FIG 15 anti-hyperalgesic effects of NAI-112a/b in the sciatic nerve constriction model of peripheral neuropathy NAI-112a/b (3-30 mg/kg, intraperitoneally) reduces both mechanical (A) and thermal (B) hyperalgesia (measured in seconds) as well as mechanical allodynia (C, measured in grams) *p<0.05, p<0.01 and *p<0.001 vs vehicle, ###p<0.001 vs sham-operated mice

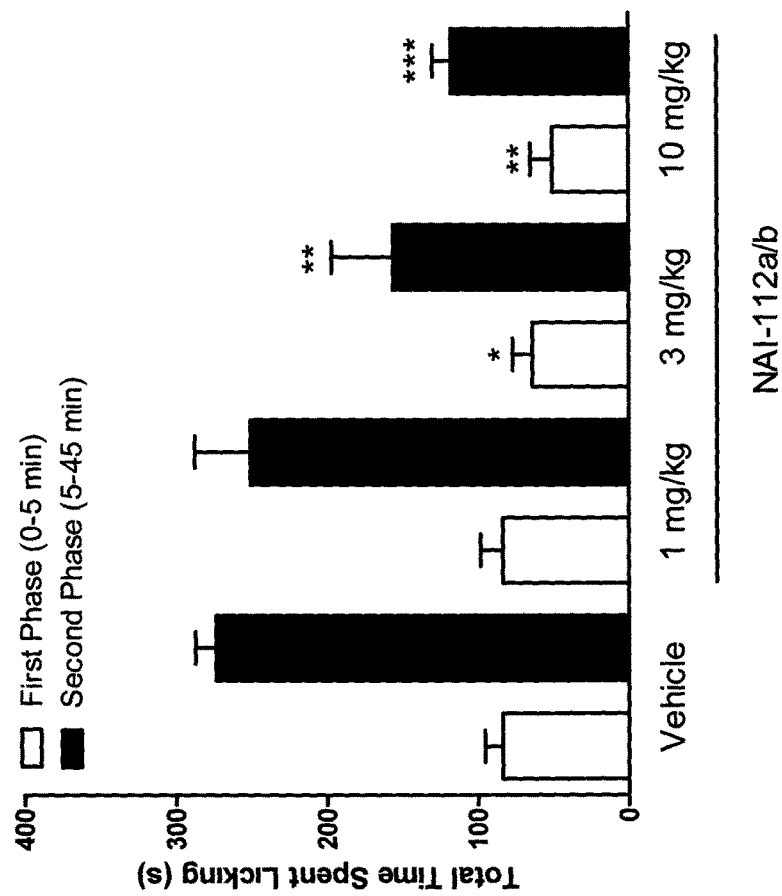
FIG 16 anti-inflammatory effects of NAI-112a/b in the formalin model in mice NAI-112a/b (1-10 mg/kg, intraperitoneally) reduces time spent in licking and biting the inflamed paw (measured in seconds) $*p<0.05$ and $**p<0.01$ vs vehicle-treated mice

SEQUENCE LISTING

```
<160> NUMBER OF SEQ ID NOS: 5

<210> SEQ ID NO 1
<211> LENGTH: 132
<212> TYPE: DNA
<213> ORGANISM: Actinoplanes sp. DSM 24059
<220> FEATURE:
<221> NAME/KEY: misc_feature
<222> LOCATION: (1)..(132)
<223> OTHER INFORMATION: gene 112-labA as isolated from Actinoplanes
      sp. DSM 24059

<400> SEQUENCE: 1
gtgcaggaga tcctggagct gcaggagctg ccgtcggcct cggccacgga ggacatgccg      60
ctggtcagca cgctcagcgt cagctcgccg tgccccggct ggccgagctc cttcacctgg     120
tcgaactgct ga                                                         132

<210> SEQ ID NO 2
<211> LENGTH: 43
<212> TYPE: PRT
<213> ORGANISM: Actinoplanes sp. DSM 24059

<400> SEQUENCE: 2

Val Gln Glu Ile Leu Glu Leu Gln Glu Leu Pro Ser Ala Ser Ala Thr
1               5                   10                  15

Glu Asp Met Pro Leu Val Ser Thr Leu Ser Val Ser Ser Pro Cys Pro
            20                  25                  30

Gly Trp Pro Ser Ser Phe Thr Trp Ser Asn Cys
        35                  40

<210> SEQ ID NO 3
<211> LENGTH: 22
<212> TYPE: PRT
<213> ORGANISM: Actinoplanes sp. DSM 24059
<220> FEATURE:
<221> NAME/KEY: MOD_RES
<222> LOCATION: (2)..(2)
<223> OTHER INFORMATION: N-terminal residue belonging to the carbacyclic
      post translationally modified amino acid labionin (Lab)
<220> FEATURE:
<221> NAME/KEY: MOD_RES
<222> LOCATION: (3)..(3)
<223> OTHER INFORMATION: Amino acid in position 3 is Dehydrobutyrine
      (Dhb) an unusual Amino Acid. Synthetase enzymes catalyze the
      dehydration of Thr residue in its peptide substrate to Dhb.
<220> FEATURE:
<221> NAME/KEY: MOD_RES
<222> LOCATION: (5)..(5)
<223> OTHER INFORMATION: central residue belonging to the carbacyclic
      post translationally modified amino acid labionin (Lab)
<220> FEATURE:
<221> NAME/KEY: MOD_RES
<222> LOCATION: (10)..(10)
<223> OTHER INFORMATION: C-terminal residue belonging to the carbacyclic
      post translationally modified amino acid labionin (Lab)
<220> FEATURE:
<221> NAME/KEY: MOD_RES
<222> LOCATION: (15)..(15)
<223> OTHER INFORMATION: N-terminal residue belonging to the carbacyclic
      post translationally modified amino acid  methyl-labionin (Me-Lab)
<220> FEATURE:
<221> NAME/KEY: MOD_RES
```

```
<222> LOCATION: (16)..(16)
<223> OTHER INFORMATION: Amino acid in position 16 is dehydroalanine
      (Dha), an unusual amino acid. Synthetase enzymes catalyze the
      dehydration of Ser residue in its peptide substrate to Dha.
<220> FEATURE:
<221> NAME/KEY: MOD_RES
<222> LOCATION: (18)..(18)
<223> OTHER INFORMATION: central residue belonging to thecarbacyclic
      post translationally modified amino acid methyl-labionin (Me-Lab)
<220> FEATURE:
<221> NAME/KEY: MOD_RES
<222> LOCATION: (22)..(22)
<223> OTHER INFORMATION: C-terminal residue belonging to thecarbacyclic
      post translationally modified amino acid  methyl-labionin (Me-Lab)

<400> SEQUENCE: 3

Val Xaa Xaa Leu Xaa Val Ser Ser Pro Xaa Pro Gly Trp Pro Xaa Xaa
1               5                  10                  15

Phe Xaa Trp Ser Asn Xaa
            20

<210> SEQ ID NO 4
<211> LENGTH: 22
<212> TYPE: PRT
<213> ORGANISM: Actinoplanes sp. DSM24059
<220> FEATURE:
<221> NAME/KEY: MOD_RES
<222> LOCATION: (2)..(2)
<223> OTHER INFORMATION: N-terminal residue belonging to the carbacyclic
      post translationally modified amino acid labionin (Lab)
<220> FEATURE:
<221> NAME/KEY: MOD_RES
<222> LOCATION: (3)..(3)
<223> OTHER INFORMATION: Amino acid in position 3 is Dehydrobutyrine
      (Dhb) an unusual Amino Acid. Synthetase enzymes catalyze the
      dehydration of Thr residue in its peptide substrate to Dhb.
<220> FEATURE:
<221> NAME/KEY: MOD_RES
<222> LOCATION: (5)..(5)
<223> OTHER INFORMATION: central residue belonging to thecarbacyclic
      post translationally modified amino acid labionin (Lab)
<220> FEATURE:
<221> NAME/KEY: MOD_RES
<222> LOCATION: (10)..(10)
<223> OTHER INFORMATION: C-terminal residue belonging to the carbacyclic
      post translationally modified amino acid labionin (Lab)
<220> FEATURE:
<221> NAME/KEY: MOD_RES
<222> LOCATION: (15)..(15)
<223> OTHER INFORMATION: N-terminal residue belonging to the carbacyclic
      post translationally modified amino acid methyl-labionin (Me-Lab)
<220> FEATURE:
<221> NAME/KEY: MOD_RES
<222> LOCATION: (18)..(18)
<223> OTHER INFORMATION: central residue belonging to the carbacyclic
      post translationally modified amino acid methyl-labionin (Me-Lab)
<220> FEATURE:
<221> NAME/KEY: MOD_RES
<222> LOCATION: (20)..(20)
<223> OTHER INFORMATION: Amino acid in position 20 is dehydroalanine
      (Dha), an unusual amino acid. Synthetase enzymes catalyze the
       dehydration of Ser residue in its peptide substrate to Dha.
<220> FEATURE:
<221> NAME/KEY: MOD_RES
<222> LOCATION: (22)..(22)
<223> OTHER INFORMATION: C-terminal residue belonging to the carbacyclic
      post translationally modified amino acid methyl-labionin (Me-Lab)

<400> SEQUENCE: 4

Val Xaa Xaa Leu Xaa Val Ser Ser Pro Xaa Pro Gly Trp Pro Xaa Ser
1               5                  10                  15

Phe Xaa Trp Xaa Asn Xaa
            20
```

<210> SEQ ID NO 5
<211> LENGTH: 1419
<212> TYPE: DNA
<213> ORGANISM: Actinoplanes sp. DSM24059
<220> FEATURE:
<221> NAME/KEY: misc_feature
<222> LOCATION: (252)..(252)
<223> OTHER INFORMATION: n is a, c, g, t or u

<400> SEQUENCE: 5

| | | | | | | |
|---|---|---|---|---|---|---|
| gcggcgtgct | aacacatgc | aagtcgagcg | gaaaggccct | tcggggtact | cgagcggcka | 60 |
| acgggtgagt | aacacgtgag | aaacctgccc | tggactttgg | gataaccctc | ggaaacgggg | 120 |
| gctaataccg | aatacgactt | accctcgcat | gggggttggt | ggaaagtttt | tcggtctggg | 180 |
| atggtctcgc | ggcctatcag | cttgttggtg | gggtaatggc | ctaccaaggc | gacgacgggt | 240 |
| agccggcctg | anagggcgac | cggccacact | gggactgaga | cacgcccag | actcctacgg | 300 |
| gaggcagcag | tggggaatat | tgcacaatgg | gcggaagcct | gatgcagcga | cgccgcgtga | 360 |
| gggatgacgg | ccttcgggtt | gtaaacctct | ttcagcaggg | acgaagcgca | agtgacggta | 420 |
| cctgcagaag | aagcgccggc | caactacgtg | ccagcagccg | cggtaagacg | tagggcgcga | 480 |
| gcgttgtccg | gatttattgg | gcgtaaagag | ctcgtaggcg | gcttgtcgcg | tcgactgtga | 540 |
| aaacccgcgg | ctcaaccgcg | ggcctgcagt | cgatacgggc | aggctagagt | tcggtagggg | 600 |
| agactggaat | tcctggtgta | gcggtgaaat | gcgcagatat | caggaggaac | accgatggcg | 660 |
| aaggcaggtc | tctgggccga | tactgacgct | gaggagcgaa | agcgtgggga | gcgaacagga | 720 |
| ttagataccc | tggtagtcca | cgctgtaaac | gttgggcgct | aggtgtgggg | gacctctccg | 780 |
| gttctctgtg | ccgcagctaa | cgcattaagc | gccccgcctg | gggagtacgg | ccgcaaggct | 840 |
| aaaactcaaa | ggaattgacg | ggggcccgca | caagcggcgg | agcatgcgga | ttaattcgat | 900 |
| gcaacgcgaa | gaaccttacc | tgggtttgac | atcgccggaa | aactcgcaga | gatgcgggt | 960 |
| ccttcggggc | cggtgacagg | tggtgcatgg | ctgtcgtcag | ctcgtgtcgt | gagatgttgg | 1020 |
| gttaagtccc | gcaacgagcg | caaccctcgt | tcgatgttgc | cagcgcgtta | tggcggggac | 1080 |
| tcatcgaaga | ctgccgggtc | aactcggagg | aaggtgggga | tgacgtcaag | tcatcatgcc | 1140 |
| ccttatgtcc | agggcttcac | gcatgctaca | atggccggta | caaagggctg | cgataccgtg | 1200 |
| aggtggagcg | aatcccaaaa | agccggtctc | agttcggatc | ggggtctgca | actcgacccc | 1260 |
| gtgaagtcgg | agtcgctagt | aatcgcagat | cagcaacgct | gcggtgaata | cgttcccggg | 1320 |
| ccttgtacac | accgcccgtc | acgtcacgaa | agtcggcaac | acccgaagcc | ggtggcctaa | 1380 |
| cccgtaaagg | gagggagccg | tcgaaggtgg | ggctggcga | | | 1419 |

LANTIPEPTIDE

This application is the U.S. national phase of International Application No. PCT/IB2012/001373, filed 12 Jul. 2012; the entire contents of which is hereby incorporated by reference.

BACKGROUND OF THE INVENTION

Lantipeptides are peptides that are ribosomally synthesized by bacteria such as staphylococci, lactobacilli, and actinomycetes. The common structural characteristic of lantipeptides is the presence of non-canonical amino acid lanthionine, which confers conformational stability to the peptidic structure. One particular example of lantipeptides is represented by the labyrinthopeptins, which contain the carbacyclic post translationally modified amino acid labionin (Lab). Labionins are formed from two Ser residues and one Cys residue. During the biosynthesis both Serine residues are dehydrated to dehydroalanines (Dha). The C-terminal Cys residue forms a thioether bridge by addition to the central Dha generating an enolate intermediate that then adds to a second N-terminal Dha to form the labionin structure. A first labyrinthopeptin known from the state of the art is Labyrinthopeptin A2 (Meidl et al., Angew. Chem. Int. Ed. 2010, 49, 1151-1154). It consists of 18 amino acids and is strongly hydrophobic.

Labyrinthopeptin A2 has a globular structure that consists primarily of hydrophobic amino acids. Formally, the structure can be dissected in two nonapeptides. Each of these nonapeptides bears a C-terminal Cys residue that forms a disulfide bond.

WO 2008/040469 describes compounds obtainable from *Actinomadura namibiensis* (DSM6313), that are defined as labyrinthopeptins composed of a highly bridged peptidic structure, 18 amino acids long, whose sequence is XDWX-LWEXCXTGXLFAXC, wherein the two Cys residues form a disulfide bridge and each X independently represents one of the non-natural amino acids involved in the bridging linkages. The compounds are described as characterized by antibacterial activity, antiviral activity, as well as activity against neuropathic and inflammatory pain.

The invention provides novel lantipeptide compounds, methods to make such compounds and their use. These and other aspects of the invention are described herein.

DESCRIPTION OF THE INVENTION

The present invention concerns peptide compounds of microbial origin having general formula (I), their pharmaceutical acceptable salts, pharmaceutical compositions thereof and their use as a medicament.

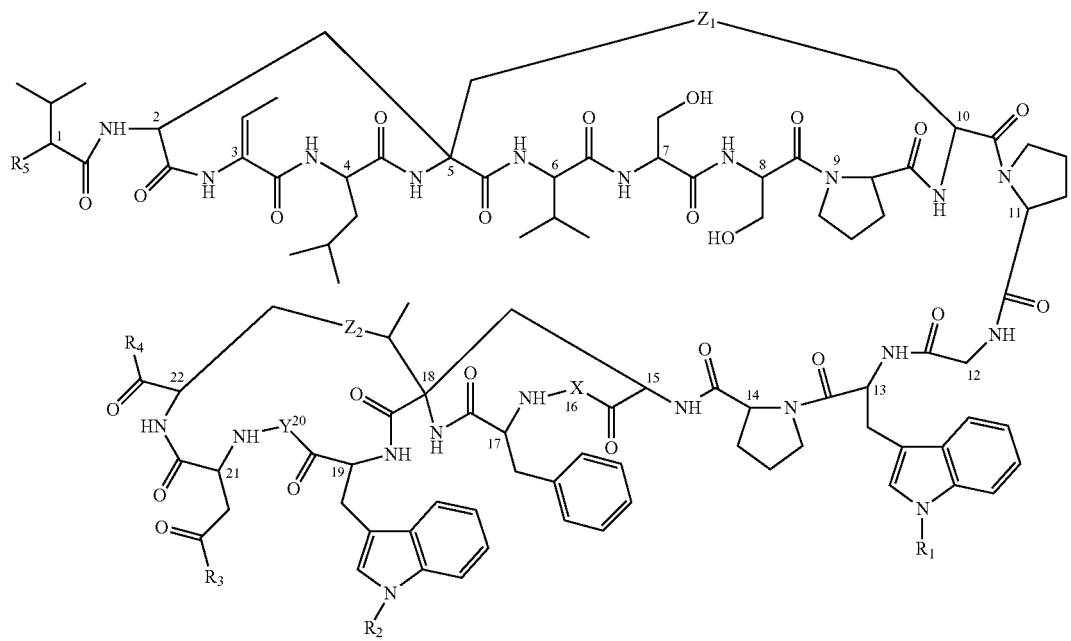

Formula (I)

Compounds of formula (I) are novel lantipeptides characterized by the presence of labionin amino acid residues. In particular, compounds of formula (I), according to the invention, are new and mainly differ from known lantipeptide compounds, according to the state of the art, for a different amino acid sequence, for the absence of a disulfide bridge due to the absence, in the structure of the compounds according to the invention, of free cysteine residues, for the presence of a derivative of labionin amino acid, methyl-labionin derivative, which has never been described before, as well as for the presence of at least a substitution on tryptophan residue. Particularly, the compounds of formula (I), according to the invention, are characterized by a different molecular charge with respect to the known compounds, are characterized by the presence of 22 amino acids instead of 18 amino acids which characterized the compounds according to the prior art. The absence of a disulfide bridge, as well as the presence of amino acid residues between positions 11 and 14 not involved in ring formation, according to the present invention, allows compounds of formula (I) to be more flexible and adopt additional conformational states with respect to known compounds. Further-more, disulfide bridges are highly subjected to redox reactions, which therefore cannot occur on compounds of formula (I) according to the present invention.

According to the present invention, and with reference to general formula (I), $R_1$ and $R_2$ are independently selected among H or a sugar moiety chosen among monosaccharides, preferably 6-deoxy hexose and their corresponding derivatives, and particularly, 6-deoxyglucose, 6-deoxygalactose (fucose), 6-deoxy-mannose (rhamnose), disaccharides (such as sucrose, lactose, maltose), trisaccharides or oligosaccharides and their corresponding deoxy derivatives, while $R_3$ and/or $R_4$ are independently selected among OH, $NH_2$, $NR_6R_7$ wherein $R_6$ and/or $R_7$ independently represent:

Hydrogen an alkyl of 1 to 20 carbon atoms (said alkyl being linear, branched, cyclic or combinations thereof);

an alkenyl of 2 to 20 carbon atoms (said alkenyl being linear, branched, cyclic or combinations thereof);

an alkynyl of 2 to 20 carbon atoms (said alkynyl being linear, branched, cyclic or combinations thereof);

a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms;

a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms a benzyl radical optionally substituted on the phenyl ring by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms a naphthyl radical optionally substituted by one or two substituents selected from halo, lower alkyl of 1 to 4 carbon atoms optionally substituted by 1 to 3 halogen atoms, and lower alkoxy of 1 to 4 carbon atoms optionally substituted by 1 to 3 halogen atoms a group of formula —$(CH_2)_nR_8$ in which n represents an integer from 2 to 8 and $R_8$ represent hydrogen or $(C_1-C_4)$ alkyl or a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms.

a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms a group of formula —$(CH_2)_nNR_9R_{10}$ in which n represents an integer from 2 to 8 and $R_9$ and/or $R_{10}$ independently represent hydrogen or $(C_1-C_4)$ alkyl or a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms a benzyl radical optionally substituted on the phenyl ring by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms $R_9$ and $R_{10}$ taken together represent a —$(CH_2)_3$—, —$(CH_2)_4$—, —$(CH_2)_2$—O—$(CH_2)_2$, —$(CH_2)_2$—S—$(CH_2)_2$ or $R_9$ and $R_{10}$ taken together with the adjacent nitrogen atom represent: a piperazine moiety which may be substituted in position 4 with a substituent selected from ($C_1$-$C_4$) alkyl, ($C_3$-$C_8$) cycloalkyl, pyridyl, benzyl and substituted benzyl wherein the phenyl moiety bears 1 or 2 substituents selected from chloro, bromo, nitro, ($C_1$-$C_4$) alkyl and ($C_1$-$C_4$) alkoxy.

Always according to the present invention, $R_5$ is selected as $NR_{11}R_{12}$ wherein $R_{11}$ and/or $R_{12}$ independently represent:

hydrogen an alkyl of 1 to 20 carbon atoms (said alkyl being linear, branched, cyclic or combinations thereof);

an alkenyl of 2 to 20 carbon atoms (said alkenyl being linear, branched, cyclic or combinations thereof);

an alkynyl of 2 to 20 carbon atoms (said alkynyl being linear, branched, cyclic or combinations thereof);

a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms;

a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms a benzyl radical optionally substituted on the phenyl ring by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms a naphthyl radical optionally substituted by one or two substituents selected from halo, lower alkyl of 1 to 4 carbon atoms optionally substituted by 1 to 3 halogen atoms, and lower alkoxy of 1 to 4 carbon atoms optionally substituted by 1 to 3 halogen atoms a group of formula —$(CH_2)_n OR_8$ in which n represents an integer from 2 to 8 and $R_8$ represent hydrogen or ($C_1$-$C_4$) alkyl or a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms.

a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms a group of formula —$(CH_2)_n NR_9 R_{10}$ in which n represents an integer from 2 to 8 and $R_9$ and/or $R_{10}$ independently represent hydrogen or ($C_1$-$C_4$) alkyl or a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms a benzyl radical optionally substituted on the phenyl ring by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms $R_9$ and $R_{10}$ taken together represent a —$(CH_2)_3$, —$(CH_2)_4$—, —$(CH_2)_2$—O—$(CH_2)_2$, —$(CH_2)_2$—S—$(CH_2)_2$ or —$R_9$ and $R_{10}$ taken together with the adjacent nitrogen atom represent: a piperazine moiety which may be substituted in position 4 with a substituent selected from $(C_1$-$C_4)$ alkyl, $(C_3$-$C_8)$ cycloalkyl, pyridyl, benzyl and substituted benzyl wherein the phenyl moiety bears 1 or 2 substituents selected from chloro, bromo, nitro, $(C_1$-$C_4)$ alkyl and $(C_1$-$C_4)$ alkoxy when $R_{11}$ or $R_{12}$ is hydrogen, $R_{12}$ or $R_{11}$ is —CO—$R_{13}$ where $R_{13}$ is selected among, $NH_2$, an alkyl of 1 to 20 carbon atoms (said alkyl being linear, branched, cyclic or combinations thereof);

an alkenyl of 2 to 20 carbon atoms (said alkenyl being linear, branched, cyclic or combinations thereof);

an alkynyl of 2 to 20 carbon atoms (said alkynyl being linear, branched, cyclic or combinations thereof);

a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms;

a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms a benzyl radical optionally substituted on the phenyl ring by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms a naphthyl radical optionally substituted by one or two substituents selected from halo, lower alkyl of 1 to 4 carbon atoms optionally substituted by 1 to 3 halogen atoms, and lower alkoxy of 1 to 4 carbon atoms optionally substituted by 1 to 3 halogen atoms a group of formula —$(CH_2)_nOR_8$ in which n represents an integer from 2 to 8 and $R_8$ represent hydrogen or $(C_1$-$C_4)$ alkyl or a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms.

a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms a group of formula

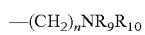

—$(CH_2)_n NR_9 R_{10}$ in which n represents an integer from 2 to 8 and $R_9$ and/or $R_{10}$ independently represent hydrogen or $(C_1-C_4)$ alkyl or a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms a benzyl radical optionally substituted on the phenyl ring by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms $R_9$ and $R_{10}$ taken together represent a —$(CH_2)_3$, —$(CH_2)_4$—, —$(CH_2)_2$—O—$(CH_2)_2$, —$(CH_2)_2$—S—$(CH_2)_2$ or —$R_9$ and $R_{10}$ taken together with the adjacent nitrogen atom represent: a piperazine moiety which may be substituted in position 4 with a substituent selected from $(C_1-C_4)$ alkyl, $(C_3-C_8)$ cycloalkyl, pyridyl, benzyl and substituted benzyl wherein the phenyl moiety bears 1 or 2 substituents selected from chloro, bromo, nitro, $(C_1-C_4)$ alkyl and $(C_1-C_4)$ alkoxy.

With reference to general formula (I), X and/or Y each represent an amino acid respectively in positions 16 and 20 of the peptide chain, that can be independently selected between Dha (dehydroalanine) and Ser (Serine). Particularly, in a preferred embodiment of the invention, in the position 16 there is a Dha residue, while in the position 20 there is a Ser residue. Always according to a preferred embodiment of the invention, in the position 16 there is a Ser residue, while in the position 20 there is a Dha residue.

$Z_1$ and $Z_2$ are independently chosen between the groups S, S—O—, S=O, O—S=O, and O=S=O.

The term "$(C_1-C_{20})$ alkyl" represents straight or branched alkyl chains of 1 to 20 carbon atoms such as, for example: methyl, ethyl, propyl, butyl, 1-methylpropyl, hexyl, octyl, decyl.

Particularly, according to the present invention, the term alkyl of 1 to 20 carbon atoms (said alkyl being linear, branched, cyclic or combinations thereof) means that said alkyl can be further substituted with a cyclic alkylic structure, an example within the scope of the present invention being, for example, —$CH_2$-cyclohexane. The same is intended for the terms alkenyl of 2 to 20 carbon atoms (said alkenyl being linear, branched, cyclic or combinations thereof) and alkynyl of 2 to 20 carbon atoms (said alkynyl being linear, branched, cyclic or combinations thereof).

The term "$(C_1-C_4)$ alkyl" represents straight or branched alkyl chains of 1 to 4 carbon atoms such as: methyl, ethyl, propyl, 1-methylethyl, butyl, 1-methylpropyl or 1,1-dimethylethyl.

The term "$(C_3-C_8)$ cycloalkyl" represents a cycloalkyl group selected from cyclopropyl, cyclobutyl, cyclopentyl, cyclohexyl and cycloheptyl, ciclooctyl.

The term "$(C_1-C_4)$ alkoxy" represents a straight or branched alkoxy chain of 1 to 4 carbon atoms such as methoxy, ethoxy, propoxy, 1-methylethoxy, butoxy, 1-methylpropoxy and 1,1-dimethylethoxy.

The term sugar moiety as used in this application is intended as chosen between monosaccharides (such as glucose, mannose, galactose), disaccharides (such as sucrose, lactose, maltose), trisaccharides or oligosaccharides. Particularly preferred are 6-deoxy hexose, and particularly, 6-deoxyglucose, 6-deoxygalactose, 6-deoxymannose, disaccharides (such as sucrose, lactose, maltose), trisaccharides or oligosaccharides and their corresponding deoxy derivatives.

Particularly, according to the present invention, a preferred substitution $R_1$ and/or $R_2$ of the tryptophan residue is a sugar moiety chosen among monosaccharides, preferably 6-deoxy hexose, and particularly, 6-deoxyglucose, 6-deoxygalactose (fucose), 6-deoxy-mannose (rhamnose), disaccharides (such as sucrose, lactose, maltose), trisaccharides or oligosaccharides and their corresponding deoxy derivatives. More preferably the sugar moiety is selected as a 6-deoxy hexose having the following formula (II):

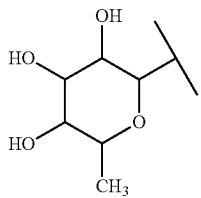

Formula (II)

The invention also relates to optically pure compounds and stereoisomeric mixtures of compounds of formula (I), such as enantiomeric mixtures and diastereomeric mixtures.

Unless otherwise indicated, the stereocenters in the compounds of formula (I) can be present in the R configuration and/or in the S configuration.

According to another preferred embodiment of the invention, $Z_1$ and $Z_2$ are independently chosen as S.

According to one preferred embodiment of the invention, X in position 16 is Dha, Y in position 20 is Ser, $Z_1$ and $Z_2$ are S, $R_1$ is 6-deoxy hexose of formula (II) and $R_2$ is H, $R_4$ is OH and $R_3$ is $NH_2$, $R_5$ is $NR_{11}R_{12}$ where $R_{11}$ and $R_{12}$ are H. This preferred compound of the invention is called NAI-112a.

According to another preferred embodiment of the invention, X in position 16 is Ser, Y in position 20 is Dha, $Z_1$ and $Z_2$ are S, $R_1$ is 6-deoxy hexose of formula (II) and $R_2$ is H, $R_4$ is OH and $R_3$ is $NH_2$, $R_5$ is $NR_{11}R_{12}$ where $R_{11}$ and $R_{12}$ are H. This compound of the invention is called NAI-112b.

According to another preferred embodiment of the invention, X in position 16 is Dha, Y in position 20 is Ser, $Z_1$ and $Z_2$ are S, $R_1$ is 6-deoxy hexose of formula (II) and $R_2$ is H, $R_4$ is OH and $R_3$ is OH, $R_5$ is $NR_{11}R_{12}$ where $R_{11}$ and $R_{12}$ are H. This preferred compound of the invention is called NAI-112c.

According to another preferred embodiment of the invention, X in position 16 is Ser, Y in position 20 is Dha, $Z_1$ and $Z_2$ are S, $R_1$ is 6-deoxy hexose of formula (II) and $R_2$ is H, $R_4$ is OH and $R_3$ is OH, $R_5$ is $NR_{11}R_{12}$ where $R_{11}$ and $R_{12}$ are H. This compound of the invention is called NAI-112d.

According to another preferred embodiment of the invention, X in position 16 is Dha, Y in position 20 is Ser, $Z_1$ and $Z_2$ are S, $R_1$ is 6-deoxy hexose of formula (II) and $R_2$ is H, $R_4$ is $NR_6R_7$ where $R_6$ is H and $R_7$ is —$(CH_2)_n NR_9R_{10}$ with n=3, $R_9$=$R_{10}$=$CH_3$, $R_3$ is $NH_2$, $R_5$ is $NR_{11}R_{12}$ where $R_{11}$ and $R_{12}$ are H. This preferred compound of the invention is called NAI-112e.

According to another preferred embodiment of the invention, X in position 16 is Ser, Y in position 20 is Dha, $Z_1$ and $Z_2$ are S, $R_1$ is 6-deoxy hexose of formula (II) and $R_2$ is H, $R_4$ is $NR_6R_7$ where $R_6$ is H and $R_7$ is —$(CH_2)_n NR_9R_{10}$ with n=3, $R_9$=$R_{10}$=$CH_3$, $R_3$ is $NH_2$, $R_5$ is $NR_{11}R_{12}$ where $R_{11}$ and $R_{12}$ are H. This preferred compound of the invention is called NAI-112f.

Always according to the invention, another preferred embodiment is the following, where X in position 16 is Dha, Y in position 20 is Ser, $Z_1$ and $Z_2$ are S, $R_1$ is 6-deoxy hexose of formula (II) and $R_2$ is H, $R_4$ is $NR_6R_7$ where $R_6$ is H and $R_7$ is benzyl, $R_3$ is $NH_2$, $R_5$ is $NR_{11}R_{12}$ where $R_{11}$ and $R_{12}$ are H. This preferred compound of the invention is called NAI-112g.

Another preferred embodiment is the following, where X in position 16 is Ser, Y in position 20 is Dha, $Z_1$ and $Z_2$ are S, $R_1$ is 6-deoxy hexose of formula (II) and $R_2$ is H, $R_4$ is $NR_6R_7$ where $R_6$ is H and $R_7$ is benzyl, $R_3$ is $NH_2$, $R_5$ is $NR_{11}R_{12}$ where $R_{11}$ and $R_{12}$ are H. This preferred compound of the invention is called NAI-112h.

A preferred embodiment of the present invention is a compound of formula (I) where X in position 16 is Dha, Y in position 20 is Ser, $Z_1$ and $Z_2$ are S, $R_1$ is 6-deoxy hexose of formula (II) and $R_2$ is H, $R_4$ is $NR_6R_7$ where $R_6$ is H and $R_7$ is benzyl, $R_3$ is $NR_6R_7$ where $R_6$ is H and $R_7$ is benzyl, $R_5$ is $NR_{11}R_{12}$ where $R_{11}$ and $R_{12}$ are H. This preferred compound of the invention is called NAI-112i.

Another preferred embodiment of the present invention is a compound of formula (I) where X in position 16 is Ser, Y in position 20 is Dha, $Z_1$ and $Z_2$ are S, $R_1$ is 6-deoxy hexose of formula (II) and $R_2$ is H, $R_4$ is $NR_6R_7$ where $R_6$ is H and $R_7$ is benzyl, $R_3$ is $NR_6R_7$ where $R_6$ is H and $R_7$ is benzyl, $R_5$ is $NR_{11}R_{12}$ where $R_{11}$ and $R_{12}$ are H. This preferred compound of the invention is called NAI-112l.

According to a further preferred embodiment of the present invention, X in position 16 is Dha, Y in position 20 is Ser, $Z_1$ and $Z_2$ are S, $R_1$ is 6-deoxy hexose of formula (II) and $R_2$ is H, $R_4$ is OH, $R_3$ is $NH_2$, $R_5$ is $NR_{11}R_{12}$ where $R_{11}$ is H and $R_{12}$ is selected among an alkyl of 1 to 20 carbon atoms (said alkyl being linear, branched, cyclic or combinations thereof), particularly is selected as —$CH_2$-cyclohexane. This preferred compound of the invention is called NAI-112m.

According to a further preferred embodiment of the present invention, X in position 16 is Ser, Y in position 20 is Dha, $Z_1$ and $Z_2$ are S, $R_1$ is 6-deoxy hexose of formula (II) and $R_2$ is H, $R_4$ is OH, $R_3$ is $NH_2$, $R_5$ is $NR_{11}R_{12}$ where $R_{11}$ is H and $R_{12}$ is selected among an alkyl of 1 to 20 carbon atoms (said alkyl being linear, branched, cyclic or combinations thereof), particularly is selected as —$CH_2$-cyclohexane. This preferred compound of the invention is called NAI-112n.

According to another preferred embodiment of the present invention, X in position 16 is Dha, Y in position 20 is Ser, $Z_1$ and $Z_2$ are S, $R_1$ is the compound having the following formula (III):

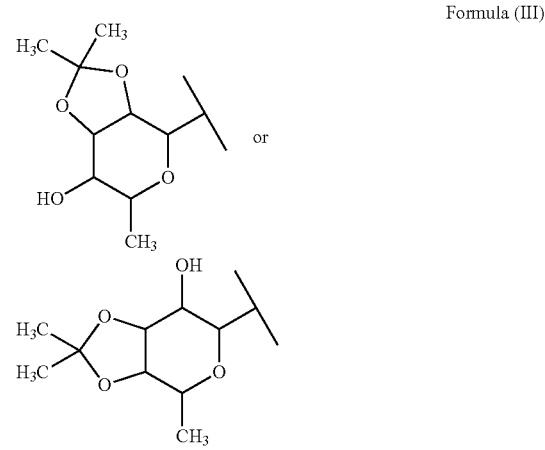

Formula (III)

$R_2$ is H, $R_4$ is OH, $R_3$ is $NH_2$, $R_5$ is $NR_{11}R_{12}$ where $R_{11}$ and $R_{12}$ are H. This preferred compound of the invention is called NAI-112o.

According to another preferred embodiment of the present invention, X in position 16 is Ser, Y in position 20 is Dha, $Z_1$ and $Z_2$ are S, $R_1$ is the compound having the following formula (III):

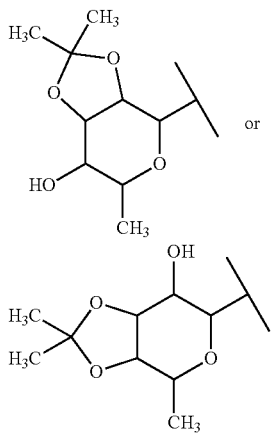

Formula (III)

$R_2$ is H, $R_4$ is OH, $R_3$ is $NH_2$, $R_5$ is $NR_{11}R_{12}$ where $R_{11}$ and $R_{12}$ are H. This preferred compound of the invention is called NAI-112p.

According to one preferred embodiment of the invention, X in position 16 is Dha, Y in position 20 is Ser, $Z_1$ and $Z_2$ are S, $R_1$ is H and $R_2$ is H, $R_4$ is OH and $R_3$ is $NH_2$, $R_5$ is $NR_{11}R_{12}$ where $R_{11}$ and $R_{12}$ are H. This preferred compound of the invention is called NAI-112q.

According to one preferred embodiment of the invention, X in position 16 is Ser, Y in position 20 is Dha, $Z_1$ and $Z_2$ are S, $R_1$ is H and $R_2$ is H, $R_4$ is OH and $R_3$ is $NH_2$, $R_5$ is $NR_{11}R_{12}$ where $R_{11}$ and $R_{12}$ are H. This preferred compound of the invention is called NAI-112r.

According to one preferred embodiment of the invention, X in position 16 is Dha, Y in position 20 is Ser, $Z_1$ and $Z_2$ are S, $R_1$ is 6-deoxy hexose of formula (II) and $R_2$ is H, $R_4$ is $NR_6R_7$ where $R_6$ is H and $R_7$ is —$(CH_2)_nNR_9R_{10}$ with n=2, $R_9$=$R_{10}$=H, $R_3$ is $NH_2$, $R_5$ is $NR_{11}R_{12}$ where $R_{11}$ and $R_{12}$ are H. This preferred compound of the invention is called NAI-112s.

According to one preferred embodiment of the invention, X in position 16 is Ser, Y in position 20 is Dha, $Z_1$ and $Z_2$ are S, $R_1$ is 6-deoxy hexose of formula (II) and $R_2$ is H, $R_4$ is $NR_6R_7$ where $R_6$ is H and $R_7$ is —$(CH_2)_nNR_9R_{10}$ with n=2, $R_9$=$R_{10}$=H, $R_3$ is $NH_2$, $R_5$ is $NR_{11}R_{12}$ where $R_{11}$ and $R_{12}$ are H. This preferred compound of the invention is called NAI-112t.

It is also object of the present invention a process for the preparation of the novel compounds having general formula (I). The process for preparing compounds of formula (I) includes culturing Actinoplanes sp. hereinafter identified as Actinoplanes sp. DSM 24059 (deposited on 29 Sep. 2010 with the Deutsche Sammlung von Mikroorganismen and Zellkulturen GmbH (DSMZ) with accession number DSM24059) or a variant or mutant thereof maintaining the ability to produce said compounds of formula (I), recovering the compounds of formula (I) from the mycelium and/or from the fermentation broth and isolating the pure substance by chromatographic means. The process optionally comprises a further step wherein compounds of formula (I) are chemically modified by semi-synthesis and/or converted into a physiologically tolerated salt.

It is also object of the present invention the DNA sequence, as defined by sequence SEQ ID NO: 1

```
GTGCAGGAGA TCCTGGAGCT GCAGGAGCTG CCGTCGGCCT

CGGCCACGGA GGACATGCCG CTGGTCAGCA CGCTCAGCGT

CAGCTCGCCG TGCCCCGGCT GGCCGAGCTC CTTCACCTGG

TCGAACTGCT GA
``` which represents the gene 112-labA as isolated from Actinoplanes sp. DSM 24059.

The amino acid sequence of the precursor polypeptide, encoded by said SEQ ID NO: 1, is provided in SEQ ID NO: 2

```
VQEILELQELPSASATEDMPL VSTLSVSSPCPGWPSSFTWSNC
``` as used by Actinoplanes sp. DSM 24059 to produce the compound of general formula (I) wherein X in position 16 is Dha, Y in position 20 is Ser, $Z_1$ and $Z_2$ are S, $R_1$ is 6-deoxy hexose of formula (II), $R_2$ is H, $R_4$ is OH, $R_3$ is $NH_2$ and $R_5$ is $NR_{11}R_{12}$, where $R_{11}$ and $R_{12}$ are H (NAI-112a); or the compound of general formula (I) wherein X in position 16 is Ser, Y in position 20 is Dha, $Z_1$ and $Z_2$ are S, $R_1$ is 6-deoxy hexose of formula (II), $R_2$ is H, $R_4$ is OH, $R_3$ is $NH_2$ and $R_5$ is $NR_{11}R_{12}$, where $R_{11}$ and $R_{12}$ are H (NAI-112b).

According to the present invention, the terms "lantipeptide NAI-112a/b", or simply "NAI-112a/b" are referred, unless otherwise specified, to the above described novel compounds of general formula (I) above described. NAI-112a and NAI-112b are also identified with sequence ID number 3 and 4.

Always according to the present invention, amino acid sequence of NAI-112a is provided in SEQ ID NO: 3

```
Val Xaa Xaa Leu Xaa Val Ser Ser Pro Xaa Pro

Gly Trp Pro Xaa Xaa Phe Xaa Trp Ser Asn Xaa
``` wherein the amino acid, indicated as Xaa, in the position 2 is the N-terminal residue belonging to the carbacyclic post translationally modified amino acid labionin (Lab), the amino acid in the position 3 is Dehydrobutyrine (Dhb), the amino acid in the position 5 is the central residue belonging to the carbacyclic post translationally modified amino acid labionin (Lab), the amino acid in the position 10 is the C-terminal residue belonging to the carbacyclic post translationally modified amino acid labionin (Lab), the amino acid in the position 15 is the N-terminal residue belonging to the carbacyclic post translationally modified amino acid methyl-labionin (Me-Lab), the amino acid in the position 16 is dehydroalanine (Dha), the amino acid in the position 18 is central residue belonging to the carbacyclic post translationally modified amino acid methyl-labionin (Me-Lab), the amino acid in the position 22 is the C-terminal residue belonging to the carbacyclic post translationally modified amino acid methyl-labionin (Me-Lab).

Always according to the present invention, amino acid sequence of NAI-112b is provided in SEQ ID NO: 4

```
Val Xaa Xaa Leu Xaa Val Ser Ser Pro Xaa Pro

Gly Trp Pro Xaa Ser Phe Xaa Trp Xaa Asn Xaa
``` wherein the amino acid, indicated as Xaa, in the position 2 is the N-terminal residue belonging to the carbacyclic post translationally modified amino acid labionin (Lab), the amino acid in the position 3 is Dehydrobutyrine (Dhb), the amino acid in the position 5 is the central residue belonging to the carbacyclic post translationally modified amino acid labionin (Lab), the amino acid in the position 10 is the C-terminal residue belonging to the carbacyclic post translationally modified amino acid labionin (Lab), the amino acid in the position 15 is the N-terminal residue belonging to the carbacyclic post translationally modified amino acid methyl-labionin (Me-Lab), the amino acid in the position 18 is central residue belonging to the carbacyclic post translationally modified amino acid methyl-labionin (Me-Lab), the amino acid in the position 20 is dehydroalanine (Dha), the amino acid in the position 22 is the C-terminal residue belonging to the carbacyclic post translationally modified amino acid methyl-labionin (Me-Lab).

The present invention also concerns a process for the preparation of compounds of formula (I) characterized in that it comprises at least one additional step of a condensation reaction between at least a starting compound of formula (I) wherein at least one $R_3$ or $R_4$ is OH, and at least a selected amine of general formula $NR_6R_7$, wherein $R_6$ and $R_7$ are defined as above, in the presence of a condensing agent.

The reaction is carried out in the presence of a condensing agent, in the presence of a solvent. Preferred inert organic aprotic solvents useful for the condensation reaction are those solvents which do not interfere with the reaction course and are capable of at least partially solubilizing the starting material. For example compounds chosen among those previously indicated in Formula (I). Solvents can be chosen among organic amides, ethers of glycols and polyols, phosphoramide derivatives, sulfoxides. Preferably, solvents are chosen among: dimethylformamide, dimethoxyethane, hexamethylphosphoroamide, dimethylsulphoxide, dioxane, N-methylpyrrolidone and mixtures thereof.

Preferably, dimethylformamide (DMF) is employed. The condensing agent according to the present invention is one suitable for forming amide bonds in organic compounds and, in particular, in peptides. Representative examples of condensing agents are diisopropylcarbodiimide (DIC), dicyclohexylcarbodiimide (DCC) with or without or hydroxybenzotriazole (HOBT), N,N,N',N'-tetramethyl-O-(benzotriazol-1-yl)uroniumtetrafluoroborate (TBTU), N,N,N',N'-tetramethyl-O-(7oxabenzotriazol-1-yl)uranium hexafluorophosphate (HATU), benzotriazolyl-oxy-tris-(dimethylamino)phosphoniumhexafluorophosphate (HBTU), benzotriazolyloxy-tris-(pyrrolidino)phosphoniumhexafluorophosphate (PyBOP) and (C1-C4) alkyl, phenyl or heterocyclic phosphorazidates such as diphenylphosphorazidate, dimorpholyl-phosphorazidate. The preferred condensing agent is PyBOP. The condensing agent is generally employed in a slight molar excess, such as from 2.2 to 5; preferably the molar excess of condensing agent is about 2.5 times the molar amount of lantipeptide starting compounds of formula (I). According to the present method, the amine is normally used in slight molar excess with respect to the compound of formula (I). In general, a 2 to 40-fold molar excess of the selected amine is used, while a 15-30 fold molar excess is preferred. When the amine $NR_6R_7$ is used as a corresponding salt, for example the hydrochloride salt, it is necessary to add a suitable base in at least a molar proportion to obtain the free base of the amine $NR_6R_7$ which reacts with compounds of formula (I). In this case, an excess of the base is generally preferred. It is convenient to add a salt-forming base to the reaction mixture in an at least equimolar amount, and preferably in about 1.2 fold molar excess with respect to the amine $HNR_6R_7$. Examples of said salt-forming bases are tertiary organic aliphatic or alicyclic amines such as trimethylamine, triethylamine (TEA), N-methylpyrrolidine or heterocyclic bases such as picoline and the like, alkali metals (e.g. sodium and potassium) hydrogen carbonates and carbonates. The reaction temperature will vary considerably depending on the specific starting materials and reaction conditions. In general, it is preferred to conduct the amidation reaction at temperature from 0° C. to 50° C. preferably at room temperature. Also the reaction time varies considerably, depending on the other reaction parameters; in general the condensation is completed in about 1-4 h. When the amine $HNR_6R_7$ contains a further primary amino group it might be protected, if necessary, as known in the art, in order to get the desired product. Any typical protecting group of the amino rest, which is resistant to the conditions applied during the process of this invention and may be readily removed under conditions which do not affect the stability of the lantipeptide of formula (I) core portion can be utilized here. Suitable protecting groups of the amino function can be selected, for instance, from the groups described in: T. W. Greene, "Protective Groups in Organic Synthesis", J. Wiley, N. Y., 1981. In particular, in this case, those protecting groups, which are formed by acylating the amino moiety, are preferred. The protecting groups employed in the process herein described are those generally employed in peptides synthesis. Obviously, a deprotection step is then necessary to obtain the desired final product. Generally, the reaction course is monitored by HPLC according to methods known in the art. On the basis of the results of this assay it will be possible to evaluate the reaction course and decide when to stop the reaction and start working up the reaction mass according to per se known techniques which include, for instance, precipitation by addition of non-solvents, extraction with solvents, in conjunction with further common separation operations and purification, e.g. by column chromatography. According to the methodologies of the present invention as well as according to the above examples, a series of compounds can be prepared, always according to the present invention.

Another additional step might comprise a reaction between at least a starting compound of formula (I) where $R_5$ is $NR_{11}R_{12}$ where $R_{11}$ and $R_{12}$ are H, and at least a suitable carbonyl compound, in the presence of a reducing agent.

The reaction is carried out in the presence of a reducing agent, in the presence of a solvent. Preferred inert organic aprotic solvents useful for the reaction are those solvents which do not interfere with the reaction course and are capable of at least partially solubilizing the starting material. For example compounds chosen between those previously indicated in Formula (I). Solvents can be chosen among organic amides, ethers of glycols and polyols, phosphoramide derivatives, sulfoxides. Preferably, solvents are chosen between: dimethylformamide, dimethoxyethane, dimethylsulphoxide, dioxane, tetrahydrofurane, water, N-methylpyrrolidone and mixtures thereof.

Preferably, dimethylformamide (DMF) is employed. The reducing agent according to the present invention is one suitable for reducing the imine formed by condensation between the amine present on the starting compound of formula (I) wherein $R_5$ is $NR_{11}R_{12}$ with $R_{11}$ and $R_{12}$ are H and the suitable carbonyl compound. Representative examples of reducing agents are sodiumborohydride ($NaBH_4$), sodium cyanoborohydride ($NaCNBH_3$), sodium triacetoxy borohydride, litium borohydride, potassium borohydride. The preferred reducing agent is $NaCNBH_3$. The condensing agent is generally employed in a slight molar excess, such as from 2.2 to 5; preferably the molar excess of condensing agent is about 2.5 times the molar amount of lantipeptide starting compounds of formula (I). According to the present method, the carbonyl compound is normally used in slight molar excess with respect to the compound of formula (I). In general, a 2 to 40-fold molar excess of the selected carbonyl compound is used, while a 15-30 fold molar excess is preferred. In general, it is preferred to conduct the alkylation reaction at temperature from 0° C. to 50° C. preferably at room temperature. Also the reaction time varies considerably, depending on the other reaction parameters; in general the condensation is completed in about 1-4 h. When the carbonyl compound contains a further primary amino group it might be protected, as known in the art, in order to get the desired product. Any typical protecting group of the amino rest, which is resistant to the conditions applied during the process of this invention and may be readily removed under conditions which do not affect the stability of the lantipeptide of formula (I) core portion can be utilized here. Suitable protecting groups of the amino function can be selected, for instance, from the groups described in: T. W. Greene, "Protective Groups in Organic Synthesis", J. Wiley, N. Y., 1981. In particular, in this case, those protecting groups, which are formed by acylating the amino moiety, are preferred. The protecting groups employed in the process herein described are those generally employed in peptides synthesis. Obviously, a deprotection step is then necessary to obtain the desired final product. Generally, the reaction course is monitored by HPLC according to methods known in the art. On the basis of the results of this assay it will be possible to evaluate the reaction course and decide when to stop the reaction and start working up the reaction mass according to per se known techniques which include, for instance, precipitation by addition of non-solvents, extraction with solvents, in conjunction with further common separation operations and purification, e.g. by column chromatography.

Another additional step might comprise a reaction between at least a starting compound of formula (I) where $R_5$ is $NR_{11}R_{12}$ where $R_{11}$ and $R_{12}$ are H, and at least a suitable halogenated compound of formula $R_{11}X$ (or $R_{12}X$) in which X can be Cl, Br, or I eventually in the presence of a catalyst such as potassium iodide (KI).

The reaction is carried out in the presence of a catalyst agent, in the presence of a solvent. Preferred inert organic aprotic solvents useful for the reaction are those solvents which do not interfere with the reaction course and are capable of at least partially solubilizing the starting material. For example compounds chosen among those previously indicated in Formula (I). Solvents can be chosen among organic amides, ethers of glycols and polyols, phosphoramide derivatives, sulfoxides. Preferably, solvents are chosen among: dimethylformamide, dimethoxyethane, dimethylsulphoxide, dioxane, tetrahydrofurane, water, N-methylpyrrolidone and mixtures thereof.

Preferably, dimethylformamide (DMF) is employed. The halogenated compound is generally employed in a slight molar excess, such as from 2.2 to 5. According to the present method, the halogenated compound is normally used in slight molar excess with respect to the compound of formula (I). In general, a 2 to 40-fold molar excess of the selected halogenated compound is used, while a 15-30 fold molar excess is preferred. In general, it is preferred to conduct the alkylation reaction at temperature from 0° C. to 50° C. preferably at room temperature. Also the reaction time varies considerably, depending on the other reaction parameters; in general the condensation is completed in about 1-4 h. Generally, the reaction course is monitored by HPLC according to methods known in the art. On the basis of the results of this assay it will be possible to evaluate the reaction course and decide when to stop the reaction and start working up the reaction mass according to per se known techniques which include, for instance, precipitation by addition of non-solvents, extraction with solvents, in conjunction with further common separation operations and purification, e.g. by column chromatography.

According to the methodologies of the present invention as well as according to the above examples, a series of compounds can be prepared, always according to the present invention. The compounds of the present invention can be administered orally, topically or parenterally, the preferred route of administration depending on the treatment to be carried out. Depending on the route of administration, these compounds can be formulated into various dosage forms. Preparations for oral administration may be in the form of capsules, tablets, liquid solutions or suspensions. As known in the art, the capsules and tablets may contain in addition to the active ingredient conventional excipients such as diluents e.g. lactose, calcium phosphate, sorbitol and the like lubricants e.g. magnesium stearate, talc, polyethylene glycol, binding agents, e.g. polyvinylpyrrolidone, gelatin, sorbitol, tragacanth, acacia, flavoring agents, and acceptable disintegrating and wetting agents. The liquid preparations generally in the form of aqueous or oily solutions or suspensions may contain conventional additives such as suspending agents. For topical use, the compounds of formula (I) of the present invention may also be prepared in suitable forms for absorption through the mucous membranes of the nose and throat or bronchial tissues and may conveniently take the form of liquid sprays or inhalants lozenges or throat paints. For medication of the eyes, the preparation may be presented in liquid or semi-liquid form. Topical applications may be formulated in hydrophobic or hydrophilic bases as ointments, creams, lotions, paints, or powders. For rectal administration the compounds of formula (I) of the invention are administered in the form of suppositories admixed with conventional vehicles, such as, for example, cocoa butter, wax, spermaceti or polyethylenglycols and their derivatives. Compositions for injection may take such forms as suspensions, solutions, or emulsions in oily or aqueous vehicles, and may contain formulation agents such as suspending, stabilizing and/or dispersing agents. Alternatively, the active ingredient may be in powder form for reconstitution at the time of delivery with a suitable vehicle, such as sterile water. The amount of active principle to be administered depends on various factors such as the size and conditions of the subject to be treated, the route and frequency of administration, and the causative agent involved.

The present invention concerns to compounds of formula (I) for their use as medicament.

The present invention also concerns compounds of formula (I) for their use in the treatment of pain.

According to the present invention, compounds of formula (I) are used in the treatment of chronic and severe pain. Specifically, compounds of formula (I) according to the invention are suitable for inflammatory and neuropathic pain, for cancer pain and pain induced by chemotherapy treatments, for migraine, and for topical and general anaesthesia.

The compounds of the invention are generally effective at a dosage comprised between about 0.03 and about 30 mg of active ingredient per kg of body weight. Depending on the characteristics of the specific compound, pain and the patients, the effective dose can be administered in a single administration per day or divided in 2 to 4 administrations per day. Particularly desirable compositions are those prepared in the form of dosage units containing from about 30 to about 500 mg per unit.

The compounds of the present invention can also be employed in combination with other drugs, such as another analgesic agent or an agent intended to treat a second symptom or the cause of a different condition. Therefore, compositions and/or combination and/or association of the compounds of the present invention with other approved drugs fall also within the scope of the present invention.

The novel compounds of formula (I) according with the present invention, including salts, formulation and compositions thereof, can be effectively employed as the active ingredients of the analgesic preparations used in human or animal medicine for the prevention and treatment of pain.

The invention also provides the use of compounds of formula (I) or composition thereof for the manufacture of a medicament for use in a specific method of treatment or prophylaxis of the human or animal body.

Compounds of formula (I) can be administered as such or in mixtures with pharmaceutically acceptable carriers.

Preferably, compounds of formula (I) for their use as in the treatment of pain can also be administered in conjunction with other known analgesic agents such as gabapentin, pregabalin, tricyclic antidepressants (including, but not limited to, imipramine, amytryptiline, desipramine and nortryptiline), plant-derived opiates (such as morphine and codeine), synthetic opioid receptor agonists (including, but not limited to, fentanyl, oxycodone, tramadol, buprenorphine, methadone, hydromorphone, pentazocine, and pethidine) and non-steroidal analgesics (including, but not limited to, aspirin, indomethacin, ibuprofen, flurbiprofen, carprofen, sulindac, diclofenac and paracetamol).

Conjunctive therapy includes sequential, simultaneous and separate administration of the compounds of formula (I) in a way that the therapeutic effects of the first administered one has not entirely disappeared when the subsequent is administered, is also comprised in the scope of protection of the present invention.

The compounds of formula (I) of the invention, or its pharmaceutically acceptable addition salts, can be formulated into forms suitable for parenteral, oral or topical administration.

Strains and Fermentation

The production of compounds of formula (I) is achieved by cultivating an *Actinoplanes* sp. strain capable of producing it, i. e. *Actinoplanes* sp. DSM24059 or a variant or mutant thereof maintaining the ability to produce compounds of formula (I), isolating the resulting lantipeptide from the whole culture broth and/or from the separated mycelium and/or from the filtered fermentation broth, and purifying the isolated lantipeptide by chromatographic means.

According to one preferred embodiment the production of compounds of formula (I) is carried out under aerobic conditions in an aqueous nutrient medium containing easy digestible or usable sources of carbon, nitrogen, and inorganic salts. Many of the nutrient media usually employed in fermentation field can be used, however preferred carbon sources are starch, dextrin, glucose, maltose, glycerol, and the like. Preferred nitrogen sources are soybean meal, peptone, meat extract, hydrolyzed casein, tryptone, corn steep liquor, cottonseed meal, yeast extract, and the like.

Soluble salts capable of yielding sodium, potassium, iron, zinc, cobalt, magnesium, calcium, ammonium, chloride, carbonate, sulphate, phosphate, nitrate, and the like ions can be incorporated in certain media.

Preferably, the strain producing compounds of formula (I) is pre-cultured in a fermentation tube or in a shake flask, then the culture is used to inoculate jar reactors for fermentation for the production of substantial quantities of substances. The medium used for the pre-culture can be the same as that employed for larger fermentations, but other media can also be employed.

According to one preferred aspect, *Actinoplanes* sp. DSM24059 strain is grown on S1 plates (detailed information are described in Experimental part) where the strain forms bright orange colonies.

The temperature for growing strain *Actinoplanes* sp. DSM24059 producing compounds of formula (I) is 26-35° C., preferably 28-32° C. During the fermentation, lantipeptide production can be monitored by HPLC analyses. Maximum production of compounds of formula (I) generally occurs after 72 hours and before 192 hours of fermentation.

Compounds of formula (I) are thus produced by cultivating *Actinoplanes* sp. DSM24059 or a variant or mutant thereof capable of producing compounds of formula (I), and it is found in the culture broths and/or in the mycelium.

*Actinoplanes* sp. DSM240597 16S rRNA Gene Sequence

The partial sequence of the 16 rRNA gene (16S rDNA), i.e 1419 nucleotides, of strain *Actinoplanes* sp. DSM24059 is reported in SEQ ID NO: 5. This sequence is compared with those deposited in public databases, and is found to be related to the 16S rRNA gene sequences of various *Actinoplanes* strains. Even if related, the sequence is clearly different from those deposited in public databases.

As with other microorganisms, the characteristics of strain producing lantipeptide NAI-112a/b are subject to variation. For example, artificial variants and mutants of the strain can be obtained by treatment with various known mutagens, such as U.V. rays, and chemicals such as nitrous acid, N-methyl-N'-nitro-N-nitrosoguanidine, and many others. All natural and artificial variants and mutants of strain *Actinoplanes* sp. DSM24059 are capable of producing lantipeptide NAI-112a/b.

SEQ ID NO: 5 (16S rRNA Gene of Strain *Actinoplanes* sp. DSM24059)

```
  1 GCGGCGTGCT TAACACATGC AAGTCGAGCG GAAAGGCCCT

TCGGGGTACT

51 CGAGCGGCKA ACGGGTGAGT AACACGTGAG AAACCTGCCC

TGGACTTTGG

101 GATAACCCTC GGAAACGGGG GCTAATACCG AATACGACTT

ACCCTCGCAT

151 GGGGGTTGGT GGAAAGTTTT TCGGTCTGGG ATGGTCTCGC

GGCCTATCAG

201 CTTGTTGGTG GGGTAATGGC CTACCAAGGC GACGACGGGT

AGCCGGCCTG

251 ANAGGGCGAC CGGCCACACT GGGACTGAGA CACGGCCCAG

ACTCCTACGG

301 GAGGCAGCAG TGGGGAATAT TGCACAATGG GCGGAAGCCT

GATGCAGCGA
```

```
351 CGCCGCGTGA GGGATGACGG CCTTCGGGTT GTAAACCTCT
    TTCAGCAGGG
401 ACGAAGCGCA AGTGACGGTA CCTGCAGAAG AAGCGCCGGC
    CAACTACGTG
451 CCAGCAGCCG CGGTAAGACG TAGGGCGCGA GCGTTGTCCG
    GATTTATTGG
501 GCGTAAAGAG CTCGTAGGCG GCTTGTCGCG TCGACTGTGA
    AAACCCGCGG
551 CTCAACCGCG GGCCTGCAGT CGATACGGGC AGGCTAGAGT
    TCGGTAGGGG
601 AGACTGGAAT TCCTGGTGTA GCGGTGAAAT GCGCAGATAT
    CAGGAGGAAC
651 ACCGATGGCG AAGGCAGGTC TCTGGGCCGA TACTGACGCT
    GAGGAGCGAA
701 AGCGTGGGGA GCGAACAGGA TTAGATACCC TGGTAGTCCA
    CGCTGTAAAC
751 GTTGGGCGCT AGGTGTGGGG GACCTCTCCG GTTCTCTGTG
    CCGCAGCTAA
801 CGCATTAAGC GCCCCGCCTG GGGAGTACGG CCGCAAGGCT
    AAAACTCAAA
851 GGAATTGACG GGGGCCCGCA CAAGCGGCGG AGCATGCGGA
    TTAATTCGAT
901 GCAACGCGAA GAACCTTACC TGGGTTTGAC ATCGCCGGAA
    AACTCGCAGA
951 GATGCGGGGT CCTTCGGGGC CGGTGACAGG TGGTGCATGG
    CTGTCGTCAG
1001 CTCGTGTCGT GAGATGTTGG GTTAAGTCCC GCAACGAGCG
     CAACCCTCGT
1051 TCGATGTTGC CAGCGCGTTA TGGCGGGGAC TCATCGAAGA
     CTGCCGGGTC
1101 AACTCGGAGG AAGGTGGGGA TGACGTCAAG TCATCATGCC
     CCTTATGTCC
1151 AGGGCTTCAC GCATGCTACA ATGGCCGGTA CAAAGGGCTG
     CGATACCGTG
1201 AGGTGGAGCG AATCCCAAAA AGCCGGTCTC AGTTCGGATC
     GGGGTCTGCA
1251 ACTCGACCCC GTGAAGTCGG AGTCGCTAGT AATCGCAGAT
     CAGCAACGCT
1301 GCGGTGAATA CGTTCCCGGG CCTTGTACAC ACCGCCCGTC
     ACGTCACGAA
1351 AGTCGGCAAC ACCCGAAGCC GGTGGCCTAA CCCGTAAAGG
     GAGGGAGCCG
1401 TCGAAGGTGG GGCTGGCGA
```

Precursor Peptide Gene Sequence

A draft genome sequence of *Actinoplanes* sp. DSM24059 is obtained through 454 technology: a total of 190.000 reads are generated, yielding 74.0 Mb of sequence on 1900 assembled contigs. Blast analysis (http://blast.ncbi.nlm.nih.gov/Blast.cgi) is used to identify the gene encoding the precursor peptide of NAI-112, using a partial amino acid sequence of. the compound of formula (I), leading to the identification of the 112-labA gene, which is flanked by the gene encoding the LabKC modifying enzyme necessary for installing the labionin amino acid residues on the precursor peptide. The DNA sequence of the 112-labA, as defined by SEQ ID NO: 1, i.e 132 nucleotides, encodes the precursor peptide, 112-labA, as defined by SEQ ID NO: 2, as used by *Actinoplanes* sp. DSM 24059 to produce the compound of general formula (I) wherein X in position 16 is Dha, Y in position 20 is Ser, $Z_1$ and $Z_2$ are S, $R_1$ is 6-deoxy hexose of formula (II) and $R_2$ is H, $R_4$ is OH and $R_3$ is $NH_2$, $R_5$ is $NR_{11}R_{12}$ where $R_{11}$ and $R_{12}$ are H. (NAI-112a) or the compound of general formula (I) wherein X in position 16 is Ser, Y in position 20 is Dha, $Z_1$ and $Z_2$ are S, $R_1$ is 6-deoxy hexose of formula (II) and $R_2$ is H, $R_4$ is OH and $R_3$ is $NH_2$, is $NR_{11}R_{12}$ where $R_{11}$ and $R_{12}$ are H (NAI-112b).

The precursor peptide contains a 21-aa leader peptide, necessary for the enzymatic processing of the precursor peptide, and a 22-aa propeptide which is post-translationally modified to produce the mature lantipeptide of general formula (I). The aa sequence of 112-LabA indicates that the Ser2/Ser5/Cys10 and Ser15/Thr18 and Cys22 motifs serve as precursors for the formation of the corresponding labionin and methyl-labionin as shown in the compound of general formula (I).

SEQ_ID NO 1 (DNA Sequence Encoding the Precursor Peptide of Compound)

```
  1 GTGCAGGAGA TCCTGGAGCT GCAGGAGCTG CCGTCGGCCT
    CGGCCACGGA GGACATGCCG
 61 CTGGTCAGCA CGCTCAGCGT CAGCTCGCCG TGCCCCGGCT
    GGCCGAGCTC CTTCACCTGG
121 TCGAACTGCT GA
```

SEQ_ID NO 2 (precursor peptide of compound)
VQEILELQELPSASATEDMPL VSTLSVSSPCPGWPSSFTWSNC Extraction and Purification of Compounds of Formula (I)

Compounds of formula (I) are found almost equally distributed both in the mycelium and in the filtered fraction of the fermentation broth. The culture may be processed to separate the mycelium from the cleared broth and the mycelium may be extracted with a water-miscible solvent to obtain a solution containing the compounds of formula (I), after removal of the spent mycelium.

This mycelium extract may then be processed separately or in pool with the supernatant according to the procedures reported hereafter for the supernatant fraction. When the water-miscible solvent may cause interferences with the operations for recovering the lantipeptide from the mycelium extract, the water-miscible solvent may be removed by distillation or may be diluted with water to a non-interfering concentration.

The term "water-miscible solvent" as used in this application, is intended to have the meaning currently given in the art of this term and refers to solvents that, at the conditions of use, are miscible with water in a reasonably wide concentration range. Examples of water-miscible organic solvents that can be used in the extraction of the compounds of the invention are: lower alkanols, e.g. (C1-C3) alkanols such as methanol, ethanol, and propanol; phenyl (C1-C3) alkanols such as benzyl alcohol; lower ketones, e.g. (C3-C4) ketones such as acetone and ethyl methyl ketone; cyclic ethers such as dioxane and tetrahydrofuran; glycols and their products of partial etherification such as ethylene glycol, propylene glycol, and ethylene glycol monomethyl ether; lower amides such as dimethylformamide and diethylformamide; acetic acid dimethylsulfoxide and acetonitrile.

The recovery of the compounds of formula (I) from the supernatant of the fermentation broth of the producing microorganism is conducted according to known per se techniques which include extraction with solvents, precipitation by adding non-solvents or by changing the pH of the solution, by partition chromatography, reverse phase partition chromatography, ion exchange chromatography, molecular exclusion chromatography and the like or a combination of two or more of said techniques.

A procedure for recovering the compounds of formula (I) from the filtered fermentation broth with water-immiscible organic solvents, is followed by precipitation from the concentrated extracts, possibly by adding a precipitating agent. Also in this case, the term "water-immiscible solvent" as used in this application, is intended to have the meaning currently given in the art to said term and refers to solvents that, at the conditions of use, are slightly miscible or practically immiscible with water in a reasonably wide concentration range, suitable for the intended use.

Examples of water-immiscible organic solvents that can be used in the extraction of the compounds of the invention from the fermentation broth are: alkanols of at least four carbon atoms which may be linear, branched or cyclic such as n-butanol, 1-pentanol, 2-pentanol, 3-pentanol, 1-hexanol, 2-hexanol, 3-hexanol, 3,3-dimethyl-1-butanol, 4-methyl-1-pentanol, 3-methyl-1-pentanol, 2,2-dimethyl-3-pentanol, 2,4-dimethyl-3-pentanol, 4,4-dimethyl-2-pentanol, 5-methyl-2-hexanol, 1-heptanol, 2-heptanol, 5-methyl-1-hexanol, 2-ethyl-1-hexanol, 2-methyl-3-hexanol, 1-octanol, 2-octanol, cyclopentanol, 2-cyclopentylethanol, 3-cyclopenthyl-1-propanol, cyclohexanol, cycloheptanol, cyclooctanol, 2,3-dimethyl-cyclohexanol, 4-ethylcyclohexanol, cyclooctylmethanol, 6-methyl-5-hepten-2-ol, 1-nonanol, 2-nonanol, 1-decanol, 2-decanol, and 3-decanol; ketones of at least five carbon atoms such as methylisopropylketone, methylisobutylketone, methyl-n amylketone, methylisoamylketone and mixtures thereof. As known in the art, product extraction from the filtered fermentation broth may be improved by adjusting the pH at an appropriate value, and/or by adding a proper organic salt forming an ion pair with the lantipeptide, which is soluble in the extraction solvent. As known in the art, phase separation may be improved by salting the aqueous phase.

When, following an extraction, an organic phase is recovered containing a substantial amount of water, it may be convenient to azeotropically distill water from it. Generally, this requires adding a solvent capable of forming minimum azeotropic mixtures with water, followed by the addition of a precipitating agent to precipitate the desired product, if necessary. Representative examples of organic solvents capable of forming minimum azeotropic mixtures with water are: n-butanol, benzene, toluene, butyl ether, carbon tetrachloride, chloroform, cyclohexane, 2,5-dimethylfuran, hexane, and m-xylene; the preferred solvent being n-butanol. Examples of precipitating agents are petroleum ether, lower alkyl ethers, such as ethyl ether, propyl ether, and butyl ether, and lower alkyl ketones such as acetone.

According to an alternative procedure for recovering the compounds of formula (I), the filtered fermentation broth can be contacted with an adsorption matrix followed by elution with a polar, water-miscible solvent or a mixture thereof, concentration to an oily residue under reduced pressure, and precipitation with a precipitating agent of the type already mentioned above.

Examples of adsorption matrixes that can be conveniently used in the recovery of the compounds of the invention, are polystyrene or mixed polystyrene-divinylbenzene resins (e.g. M112 or S112, Dow Chemical Co.; Amberlite® XAD2 or XAD4, Rohm & Haas; Diaion HP 20, Mitsubishi), acrylic resins (e.g. XAD7 or XAD8, Rohm & Haas), polyamides such as polycaprolactames, nylons and cross-linked polyvinylpyrrolidones (e.g. Polyamide-CC 6, Polyamide-SC 6, Polyamide-CC 6.6, Polyamide-CC 6AC and Polyamide-SC 6AC, Macherey-Nagel & Co., Germany; PA 400, M. Woelm AG, Germany); and the polyvinylpirrolidone resin PVP-CL, (Aldrich Chemie GmbH & Co., KG, Germany) and controlled pore cross-linked dextrans (e.g. Sephadex® LH-20, Pharmacia Fine Chemicals, AB). Preferably, polystyrene resins are employed, particularly preferred being the Diaion HP 20 resin. In the case of polystyrene resins, polystyrene-divinylbenzene resins, polyamide resins or acrylic resins a preferred eluent is a water-miscible solvent or its aqueous mixtures.

The aqueous mixtures can contain buffers at appropriate pH value. Also in this case, the term "water-miscible solvent", as used in this description and claims, is intended to have the meaning currently given in the art to said term as described above.

The successive procedures for the isolation and purification of the lantipeptide compounds of formula (I) according to the invention, may be carried out on the pooled extracts from the broth supernatant and/or from the mycelium.

For example, when the portion of the lantipeptide compounds of formula (I) product contained in the filtered fermentation broth or supernatant is recovered by absorption on an absorption resin and the portion of the lantipeptide product contained in the mycelium is extracted therefrom with a water-miscible solvent, followed by adsorption onto an absorption resin, the eluted fractions from each of the two sets of absorption resins may be combined, optionally after concentration, and then further processed as a unitary crop.

Alternatively, when the two sets of absorption resins utilized for the separate extraction stages are of the same type and have the same functional characteristics, they may be pooled together and the mixture may be submitted to a unitary elution step, for instance, with a water-miscible solvent or a mixture thereof with water.

In any case, whatever may be the procedure adopted for recovering the crude compounds of formula (I), the successive purification step is usually carried out on the mixture of the crude materials resulting from the combination of the products originating from the separate extraction stages. Purification of the crude compounds of formula (I), can be accomplished by any of the known techniques but is preferably conducted by means of chromatographic procedures.

Examples of these chromatographic procedures are those reported in relation to the recovery step and include also chromatography on stationary phases such as silica gel, alumina, activated magnesium silicate and the like or reverse phase chromatography on silanized silica gel having various functional derivatization, and eluting with water miscible solvents or aqueous mixture of water-miscible solvents of the kind mentioned above.

For instance, preparative HPLC chromatography may be employed, using RP-8 or RP-18 as stationary phase and a mixture of $HCOONH_4$ buffer: $CH_3CN$ or trifluoroacetic acid (0.1%): $CH_3CN$ as eluting system. The active fractions recovered from the purification step are pooled together, concentrated under vacuum, precipitated by addition of a precipitating agent of the kind mentioned above and dried or lyophilized in single or iterative rounds.

In case the product contains residual amounts of ammonium formate or other buffering salts, these may be removed by absorption of the compounds of formula (I), on solid phase extraction column, for instance a reverse phase resin column such as SPE Superclean LCP18 Supelco (Bellefonte Pa., USA) followed by washing with distilled water and elution with an appropriate aqueous solvent mixture, e.g. methanol:water. The compounds of formula (I) are then recovered by removing the elution solvents.

Accordingly, dried preparations of purified compounds of formula (I) are obtained as a white powder. As usual in this art, the production as well as the recovery and purification steps may be monitored by a variety of analytical procedures including HPLC or HPLC coupled with mass sp

BRIEF DESCRIPTION OF THE DRAWINGS

FIG. 1A represents the low resolution spectrum of the fragmentation pattern of NAI-112a/b.

FIG. 1B represents NAI-112a/b MS full-scan high resolution spectrum showing a doubly protonated ion at m/z 1184.

FIG. 2 represents IR spectrum of NAI-112a/b in KBr.

FIG. 3 represents UV spectrum of antibiotic NAI-112a/b dissolved in acetonitrile:water FIG. 4 represents the 1H-NMR spectrum of NAI-112a/b recorded in the mixture acetonitrile-d3:D2O/H2O at 25° C. in a Bruker AMX 600 spectrometer.

FIG. 5 represents the HSQC spectrum of NAI-112a/b recorded in the mixture acetonitrile-d3:D2O at 25° C. in a Bruker AMX 600 spectrometer.

FIG. 6 represents the HMBC spectrum recorded in the mixture acetonitrile-d3:D2O at 25° C. in a Bruker AMX 600 spectrometer.

FIG. 7 represents NAI-112c/d full-scan low resolution spectrum showing a doubly protonated ion at m/z 1184.9.

FIG. 8 represents NAI-112e/f full-scan low resolution spectrum showing a doubly protonated ion at m/z 1226.2.

FIG. 9 represents NAI-112g/h full-scan low resolution spectrum showing a doubly protonated ion at m/z 1228.5.

FIG. 10 represents NAI-112i/l full-scan low resolution spectrum showing a doubly protonated ion at m/z 1273.6.

FIG. 11 represents NAI-112m/n full-scan low resolution spectrum showing a doubly protonated ion at m/z 1232.4.

FIG. 12 represents NAI-112o/p full-scan low resolution spectrum showing a doubly protonated ion at m/z 1203.9.

FIG. 13 represents NAI-112q/r full-scan low resolution spectrum showing a doubly protonated ion at m/z 1111.3.

FIG. 14 represents NAI-112s/t full-scan low resolution spectrum showing a doubly protonated ion at m/z 1205.3.

FIG. 15 represents the antihyperalgesic effects of NAI-112a/b in the sciatic nerve constriction model of peripheral neuropathy FIG. 16 represents the anti-inflammatory effects of NAI-112a/b in the formalin model in mice ectrometry.

The present invention is better illustrated by means of the examples given below which in no way limit said invention.

Example 1

Preparation of NAI-112a/NAI-112b
Fermentation Method of *ACTINOPLANES* sp. DSM24059

*Actinoplanes* sp. DSM24059 is maintained on S1 plates for 2-3 weeks at 28° C. S1 is composed of (g/L) oatmeal 60, agar 18, $FeSO_4 \times 7\ H_2O$ 0.001, $MnCl_2 \times 4\ H_2O$ 0.001, $ZnSO_4 \times 7\ H_2O$ 0.001. Solid oatmeal is suspended in the appropriate volume of distilled water, boiled for 20 min and filtered through cheesecloth. The remaining components are added, volume made up with distilled water and pH adjusted to 7.2 before sterilization at 121° C. for 20 min. The microbial content of one S1 plate is scraped and inoculated into a 500-mL Erlenmeyer flasks containing 100 mL of seed medium which is composed of (g/L) dextrose monohydrate 10, maize dextrin 24, yeast extract 5, soya peptone 5. The medium is prepared in distilled water and pH adjusted to 7.2 before sterilization at 121° C. for 20 min. The inoculated flasks are grown at 28° C., on a rotatory shaker operating at 200 rpm. After 2-3 days, 5% of this culture is inoculated into a second series of flasks containing the same fermentation medium. After 48 hours of incubation, 750 mL are transferred into a 19.5-L bioreactor containing 15 L of the production medium composed of (g/L) dextrose monohydrate 10, maltose 10, yeast extract 2, soybean meal 8, and calcium carbonate 4. The medium is prepared in distilled water and pH adjusted to 7.3 prior to sterilization at 121° C. for 25 min. Dextrose monohydrate is sterilized separately and added after cooling the fermenter. The fermentation is carried out at 30° C., with 600 rpm stirring and 0.5 vvm aeration, and the culture is harvested after 90 hours. Production of NAI-112a/NAI-112b is monitored by HPLC as described below, after extraction of the whole culture broth with twice the volume of methanol and incubating the mixture at 50° C. under stirring for one hour.

Recovery and Purification of NAI-112a/NAI-112b

The fermentation broth (2 L) is added of 2 L of methanol and the pH lowered to 4.5 by addition of AcOH (100 mL). The mixture is shaken for 1 hour at room temperature and filtered on a Buchner. The filtered solution is evaporated to reduced volume (600 mL), split into 6×100-mL portions, and each is loaded on a 10 g Flash C18 prepacked column (Isolute, Biotage) placed on a Vac Master system (Stepbio). The loaded solution is washed with acetonitrile:water 25:75 (30 mL) and eluted with acetonitrile:water 1:1 (30 mL). The eluted fractions are monitored for the presence of NAI-112a/NAI-112b by analytical HPLC method as described below, and concentrated under reduced pressure.

Crude NAI-112a/NAI-112b (120 mg), prepared as described above, is purified by medium pressure chromatography on 86 g of reverse phase C18 RediSep RF column (40-63 μm particle size, 60 Å pore size, 230-400 mesh) by using a CombiFlash RF Teledyne Isco Medium Pressure Chromatography System. The resin is previously conditioned at 60 ml/min with a mixture of phase A:phase B 8:2 (v/v), then brought to 30% of phase B in 1 min and successively eluted with a 16-min linear gradient from 30 to 50% phase B. Phase A is water with 0.05% TFA and phase B is acetonitrile with 0.05% TFA. The fractions containing NAI-112a/NAI-112b are pooled, concentrated under vacuum and lyophilized from water, yielding 57 mg of purified NAI-112a/NAI-112b.

Example 2: Alternative Recovery and Purification of NaI-112a/NaI-112b

To the fermentation broth (5 L), prepared as described in the Example 1, 1 L methanol is added and the pH lowered to 4.5 by addition of AcOH (50 mL). The mixture is shaken for 1 hour at room temperature and filtered on a Buchner. The retentate portion containing the mycelium is additioned with 1 L methanol, stirred for 3 hours and filtered to obtain 1.5 L of mycelium extract. The extract is concentrated and lyophilized recovering 260 mg of crude NAI-112a/NAI-112b.

Crude NAI-112a/NAI-112b (260 mg), prepared as described above, is purified by preparative high performance liquid chromatography by using a Waters Fraction Lynx Autopurification System, equipped with a Waters Micromass ZQ and a Waters 2996 Photodiode Array Detector. The crude is purified on a)(Bridge Prep C18 column (5 μm OBD, 19×100 mm) previously conditioned with a mixture of phase A:phase B 1:1 (v/v) and then eluted at 20 ml/min with 10 min linear gradient from 50 to 70% phase B. Phase A is water with 0.05% TFA and phase B is acetonitrile with 0.05% TFA. The fractions containing NAI-112 are pooled, concentrated under vacuum and lyophilized from water, yielding 70 mg of purified NAI-112a/NAI-112b.

A preferred analytical HPLC technique is performed on a Shimadzu instrument (LC 2010A-HT liquid chromatograph, Shimadzu Corporation, Japan) equipped with a column LiChrosphere RP18, 5μ (125×4 mm) eluted at 1 ml/min flow rate and at 50° C. temperature. Elution is with a multistep program: time=0 (10% phase B); time=20 min (50% phase B); time=21 min (80% phase B); time=25 min (80% phase B); time=26 min (10% phase B); time=35 min (10% phase B). Phase A and phase B are 0.05% TFA (v/v) in water and acetonitrile, respectively. UV detection is at 230 nm and 270 nm. Under these HPLC conditions, NAI-112a/NAI-112b show a retention time of 17.5 min.

A preferred analytical HPLC-MS technique is performed on a Agilent 1100 series liquid chromatograph equipped with a column Ascentis express Supelco RP18, 2.7μ (50×4.6 mm) eluted at 1 ml/min flow rate and at 40° C. temperature. Elution was with a multistep program: time=0 (5% phase B); time=6 min (95% Phase B); time=7 min (100% phase B); time=7.2 min (5% phase B); time=10 min (5% phase B). Phase A and phase B are 0.05% TFA (v/v) in water and acetonitrile, respectively. UV detection is at 220 nm. The effluent from the column is split in a 1:1 ratio, with one part diverted to photodiode array detector. and the remaining part diverted to the ESI interface of a Bruker Esquire3000 plus ion trap mass spectrometer.

The mass spectrometric analysis is performed under the following conditions.

Sample inlet conditions: sheat gas ($N_2$) 50 psi; dry gas 10 l/min; capillary heater 365° C.;

Sample inlet voltage settings: positive polarity; capillary voltage −4000V; end plate offset −500V;

Scan conditions: maximum ion time 200 ms; ion time 5 ms; full micro scan 3;

Segment: duration 10 min, scan events positive (100-2400 m/z).

Under these analytical HPLC-MS conditions NAI-112a/NAI-112b show retention times of 3.9 min.

Since compounds NAI-112a or NAI-112b contain acid and basic functions, they are capable of forming salts with suitable bases or acids according to conventional procedures and they may exist also in the form of inner salt. A lantipeptide, for example NAI-112a or NAI-112b, when obtained in the acid form or in the form of inner salt, may be converted into a corresponding non-toxic pharmaceutically acceptable salt with bases. Suitable salts include the alkali and alkaline earth metal salts, typically the sodium, potassium, calcium and magnesium salts, and the ammonium and substituted ammonium salts. Representative substituted ammonium salts include primary, secondary or tertiary (C1-C4) alkylammonium and hydroxy (C1-C4) alkylammonium salts and, according to an embodiment of the present invention, the benzathine, procaine, hydrabamine and similar water insoluble, non-toxic, pharmaceutically acceptable salts. Another preferred class of salts of the compounds of the present invention is represented by the basic addition salts with basic amino acids such as arginine or lysine, or aminosugars such as glucosamine and the like.

The alkali and alkaline earth metal salts are prepared according to the usual procedures commonly employed for preparing metal salts. As an example, lantipeptide NAI-112a or NAI-112b, in the acid form or in the inner salt form, is dissolved into the minimum amount of a suitable solvent, typically a lower alkanol, or a lower alkanol water mixture, the stoichiometric amount of a suitable selected base is gradually added to the obtained solution and the obtained salt is precipitated by the addition of a non-solvent. The alkali or alkaline earth metal salt, which forms is then recovered by filtration or evaporation of the solvents.

Alternatively, these salts can be prepared in a substantially anhydrous form through lyophilization; in this case aqueous solutions containing the desired salts, resulting from the salification of lantipeptide NAI-112a or NAI-112b with a suitably selected alkali or alkaline earth metal carbonate or hydroxide in such a quantity as to obtain a pH comprised between 7.0 and 8.5 are filtered from any insolubles and lyophilized.

The organic ammonium salts can be prepared substantially following the above procedure by adding the properly selected amine to a solution of compounds of formula (I) in a suitable solvent and then evaporating off the solvent and the excess of the amine reagent or by lyophilizing the concentrate solution.

The addition salts of compounds of formula (I) with acids can be also prepared. Representative and suitable acid addition salts of the compounds of the invention include those salts formed by standard reaction with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, palmitic, cholic, pamoic, mucic, glutamic, camphoric, glutaric, glycolic, phthalic, tartaric, lauric, stearic, salicylic, methanesulfonic, benzenesulfonic, sorbic, picric, benzoic, cinnamic and the like acids. The addition salts of lantipeptide NAI-112a/NAI-112b with acids can be prepared in a substantially analogues manner as that employed for the preparation of the salts with bases but using the appropriately selected acid as reagent in the place of the base.

The pharmaceutically acceptable salts so formed are also part of this invention. "Pharmaceutically acceptable" salts are useful in the therapy of warm-blooded animals.

The transformation of the non salts (or internal salts) of compounds of the invention into the corresponding addition non-toxic salts, and the reverse, i.e. transformation of an addition salt of a compounds of the invention into the non-salt form are within the ordinary technical skill and are encompassed by the present invention.

Physico-Chemical Characteristics of NAI-112a or NAI-112b

A) Mass spectrometry:

in MS experiments on a Bruker Esquire3000 plus instrument fitted with an electrospray source, using Bruker calibration mix, NAI-112a or NAI-112b gives a doubly protonated ion at m/z=1184.5 corresponding to its lowest isotope composition. The fragmentation pattern of NAI-112a or NAI-112b presents the following ions: a doubly protonated ion at m/z 1111 and monoprotonated ions at m/z 974, 1393, 1247, 907, 1460 and 1314. The electrospray conditions are: capillary temperature: 365° C.; capillary voltage: −4 kV; infusion mode 5 μl/min. The spectrum of the fragmentation pattern recorded from a 0.2 mg/ml solution in methanol/water 50/50 (v/v) with 0.1% TFA is reported in FIG. 1A.

NAI-112a or NAI-112b gives high resolution mass of the doubly protonated ion at m/z=1184.0231 in experiments on an Exactive (ThermoFisher Scientific) spectrometer fitted with a nano-ESI source and equipped with an Orbitrap Mass analyzer with a resolution of 100000 m/Δm. Mass spectrum is reported in FIG. 1B.

B) The infrared spectrum of NAI-112a or NAI-112b recorded in KBr with a Bruker FT-IR spectrophotometer model IFS 48, exhibits absorption maxima at (cmd): 3393; 2962; 1670; 1522; 1457; 1203; 1138. Infrared spectrum is reported in FIG. 2.

C) The U.V. spectrum of NAI-112a or NAI-112b, performed in 0.1% TFA in water/acetonitrile (in ratio 56:44) with a Shimadzu Diode Array detector SPD-M10A VP (Shimadzu Corporation, Japan) during a HPLC analysis, exhibits two shoulders at 229 and 281 nm. UV spectrum is reported in FIG. 3

D) 1H-NMR and 2D experiments were recorded in the mixtures $CD_3CN/D_2O$ 50/40 (v/v) with and without the addition of 50 μL of $H_2O$ at 25° C. on a Bruker AMX 600 spectrometer. If necessary a water suppression sequence is applied. As internal standard the residual signal of acetonitrile at 1.99 ppm is considered.

The 1H-NMR spectrum of NAI-112a or NAI-112b is reported in FIG. 4. 1H NMR spectrum of NAI-112 dissolved in $CD_3CN/H_2O/D_2O$ 50/10/40 (v/v) exhibits the following groups of signals (in ppm) at 600 MHz using $CD_3CN$ as internal standard (1.99 ppm), [δ=ppm, multiplicity; (attribution)]:

0.70 ($CH_3$), 0.76 ($CH_3$), 0.82 ($CH_3$), 0.87 ($CH_3$), 0.91 ($CH_3$), 0.99 ($CH_3$), 1.16 ($CH_3$), 1.46 ($CH_3$), 1.62 ($CH_3$), 1.45-1.66 ($CH_2$), 1.77-3.33 (beta and gamma CH's and $CH_2$'s), 3.37-4.99 (alpha and beta CH's and $CH_2$'s), 3.17, 3.52, 4.04, 4.55 and 5.81 (sugar aliphatic's and anomeric's protons), 4.83-5.03 (Dha beta $CH_2$), 5.80 (Dhb beta CH's), 7.04-8.59 (aromatic and peptidic NH's).

E) NAI-112a or NAI-112b exhibits the following 13C groups of signals [δ=ppm; (attribution)]: 11.8-22 (aliphatic $CH_3$'s), 22.2-40.1 (beta and gamma CH's and $CH_2$'s), 42.5-62 (alpha and beta CH's and $CH_2$'s), 108.4-137.3 (aromatic CH's and quaternary carbons), 168-176 (peptidic carbonyls). HSQC and HMBC spectra of NAI-112a or NAI-112b are reported in FIGS. 5 and 6.

Amino-Acid Composition of NAI-112a/NAI-112b

A) Determination of "Acid Resistant" Amino Acids in NAI-112a/NAI-112b

NAI-112a/NAI-112b is submitted to complete acidic hydrolysis and the amino acid components resistant to acid treatment are identified. Acid labile amino acids are not detectable with this approach.

The hydrolysate (6N HCl at 105° C. for 24 h using a Vacucell or at 160° C. for 5 min using a Biotage Initiator microwave) is analyzed by HPLC-MS after derivatization with 4-(3-isothiocyanatopyrrolidin-1-yl)-7-nitro-2,1,3-benzoxadiazole [(R)-(−)-NBD-PyNCS] in comparison with a mixture of standard amino acids similarly derivatized.

The qualitative HPLC analysis is carried out on a liquid chromatography system with simultaneous DAD and MS detection. The HPLC method employs the following conditions: an Ascentis express Supelco RP18, 2.7μ (50×4.6 mm) column, set at 40° C.; a flow rate of 1 mL/min; .phase A as 0.05% TFA in water (v/v); phase B as 0.05% TFA in acetonitrile (v/v); elution program as

| Time (min) | 0 | 6 | 7 | 7.2 | 10 |
| --- | --- | --- | --- | --- | --- |
| % B | 10 | 95 | 100 | 10 | 10 |

MS conditions are the following:

Spectrometer: Bruker Esquire3000 plus equipped with standard electrospray source.

Capillary temperature: 365° C.

Capillary voltage: −4 kV

End Plate offset: −500V

Sheat gas (N2): 50 psi.

In the HPLC/MS chromatograms obtained on the hydrolysate of NAI-112a/NAI-112b, the following amino acids are identified along with other unidentified peaks: tryptophan, glycine, proline, valine, leucine or isoleucine, phenylalanine.

N-Terminal Aminoacid Identification of NAI-112a/NAI-112b 1 mg of NAI-112a/NAI-112b is dissolved in 1.5 mL methanol. Triethylamine (50 μL) and phenylisothiocyanate (10 μL) are added and the reaction is stirred at 60° C. for 1 h. The solution is extracted with hexane:dichloromethane 8:2 (3×300 μL), evaporated to dryness, dissolved in 50% TFA in $H_2O$ (500 μL) and reacted at 60° C. for 1 h. The reaction solution is directly analysed by HPLC-MS, which shows the double charged peak of m/z 1134.9 amu corresponding to the truncated peptide after loss of the N-terminal valine.

Example 3: Synthesis of NAI-112s/NAI-112t

To a stirred solution of 10 mg of NAI-112a/NAI-112b in 1.2 mL DMF, 2 μL of ethylendiamine and 4 mg of PyBOP are added and the reaction mixture is kept under stirring at room temperature for 1 hour. The reaction is quenched by addition of 2N HCl (100 μL) until neutral pH and then diluted with water. The sample is purified by medium pressure chromatography on 4.3 g of reverse-phase C18 RediSep RF column (40-63 μm particle size, 60 Å pore size, 230-400 mesh) by using a CombiFlash RF Teledyne Isco Medium Pressure Chromatography System. The resin is previously conditioned with a mixture of phase A:phase B 7:3 (v/v) and is then eluted at 18 ml/min with 10 min linear gradient from 30% to 70% phase B. Phase A is 50 mM $HCOONH_4$ in water and phase B is acetonitrile. The fractions containing the desired amide are collected, evaporated to reduced volume and lyophilized. The obtained compound shows a doubly protonated peak at m/z 1205.3 amu.

Example 4: Synthesis of NAI-112g/NAI-112h

To a stirred solution of 30 mg of NAI-112a/NAI-112b in 3 mL of DMF, 4 μl of benzylamine and 7 mg of PyBOP are added and the reaction mixture is kept under stirring at room temperature over night. The reaction is quenched by addition of 2N HCl (100 µL) until neutral pH and then diluted with water. The sample is purified by medium pressure chromatography as described in Example 3. The obtained compound shows a doubly protonated peak at m/z 1228.5 amu.

Example 5: Synthesis of NAI-112i/NAI-112l

The pH of a stirred solution of 30 mg of NAI-112a/NAI-112b in 3 mL of DMF is adjusted to 8.5 with 0.1 M NaOH. Successively, 4 µL of benzylamine and 7 mg of PyBOP are added and the reaction mixture is kept under stirring at room temperature over night. The reaction is quenched by addition of 2N HCl (100 µL) until neutral pH and then diluted with water. The sample is purified by medium pressure chromatography as described in Example 3. The obtained compound shows a doubly protonated peak at m/z 1273.6 amu.

Example 6: Synthesis of NAI-112o/NAI-112p 30 mg of NAI-112a/NAI-112b are dissolved in 200 µL of DMF and 1.8 mL of acetone. To this solution 3 mg of p-toluensulfonic acid are added and the reaction mixture is kept under stirring at 45° C. for 5 hour after which HPLC-MS monitor shows a conversion of 50%. The sample is purified by medium pressure chromatography as described in Example 3. The obtained compound shows a doubly protonated peak at m/z 1203.9 amu.

Example 7: Synthesis of NAI-112q/NAI-112r 50 mg of NAI-112a/NAI-112b are dissolved in 5 mL of 50% TFA and stirred at room temperature for 1 week. After this time an acceptable amount of the desired compound is detected by HPLC-MS analysis and the reaction is quenched by neutralizing the pH with 1 M NaOH (100 µL). The sample is purified by medium pressure chromatography as described in Example 3. The obtained compound shows a doubly protonated peak at m/z 1111.3 amu.

Example 8: Synthesis of NAI-112e/NAI-112f

To a stirred solution of 20 mg of NAI-112a/NAI-112b in 2 mL of DMF, 3 µL of 3-(dimethylamino)-1-propylamine and 9 mg of PyBOP are added and the reaction mixture is kept under stirring at room temperature for 3 hours. The reaction is quenched by addition of 2N HCl (100 µL) until neutral pH and then diluted with water. The sample is purified by medium pressure chromatography as described in Example 3. The obtained compound shows a doubly protonated peak at m/z 1225.9 amu.

Example 9: Synthesis of NAI-112m/NAI-112n

To a stirred solution of 27 mg of NAI-112a/NAI-112b in 2 mL of DMF dry, 9 µL of cyclohexane carboxaldehyde is added and the reaction mixture is kept under stirring at room temperature for 30 min. Successively, 1 mg of NaCNBH$_3$ is added and the mixture is kept at room temperature under stirring for 20 min. The reaction is quenched by dilution with water. The sample is purified by medium pressure chromatography as described in Example 3. The obtained compound shows a doubly protonated peak at m/z 1232.4 amu.

Example 10: Synthesis of NAI-112c/NAI-112d

A fermentation broth (2 L) of *Actinoplanes* sp. DSM24059 prepared as described in Example 1 is brought to pH 8 with 0.1M NaOH after harvesting. The recovery of the product is conducted as described either in Example 1 or in Example 2. The obtained compound shows a doubly protonated peak at m/z 1184.9 amu.

Example 11: Analgesic Activity on Nociceptive Pan

Sciatic nerve ligations are performed according to Bennett and Xie (1988). Mice are anesthetized with 2-3% isoflurane, and the left sciatic nerve is exposed at mid-thigh level through a small incision and tied at two distinct sites (spaced at a 2-mm interval) with a silk thread. The wound is closed with a single muscle suture and skin clips, and dusted with streptomycin. In sham-operated animals (negative control), the nerve is exposed but not tied.

All experiments are performed 'blind' in a quiet room, and scientists running the experiments are not aware of the treatment protocol at the time of the test (blind procedure). We evaluate mechanical hyperalgesia by measuring the latency (in s) to withdraw the paw from a constant mechanical pressure exerted onto the dorsal surface. A 15-g calibrated glass cylinder (diameter=10 mm) chambered to a conical point (diameter=3 mm) is used to exert the mechanical force. The weight is suspended vertically between two rings attached to a stand and is free to move vertically. A cutoff time of 180 s is used. Withdrawal thresholds are measured on both ipsilateral (experimental) and contralateral (control) paws at various times after drug administration. Thermal hyperalgesia is assessed by the method of Hargreaves et al. (1988) measuring the latency to withdraw the hind paw from a focused beam of radiant heat (thermal intensity: infrared 3.0) applied to the plantar surface using a plantar test apparatus (Ugo Basile, Italy). The cutoff time is set at 30 s. Withdrawal latency is measured on the injured ipsilateral paw.

Tactile allodynia (DPA): Animals are placed individually in a small enclosed testing arena (20 cm×18.5 cm×13 cm) with a wire mesh floor for 5 min. The DPA device is positioned beneath the animal, so that the filament is directly under the plantar surface of the foot to be tested. When a trial is initiated, the device raises the filament to touch the foot and progressively increases force until the animal withdraws its foot, or until it reaches a maximum of 5 g of force. The DPA automatically records the force at which the foot is withdrawn and the withdrawal latency (latency and maximum force are directly related, because the device progressively increases force until withdrawal occurs).

NAI-112a/b is administered at the doses of 3, 10 and 30 mg/kg, intraperitoneally, and pain behavior is measured 3 hours after dosing. As shown in FIG. 15, a single application of NAI-112a/b is sufficient to cause a rapid reversal of established hyperalgesia and allodynia. FIG. 15 shows: anti-hyperalgesic effects of NAI-112a/b in the sciatic nerve constriction model of peripheral neuropathy. NAI-112a/b (3-30 mg/kg, intraperitoneally) reduces both mechanical (A) and thermal (B) hyperalgesia (measured in seconds) as well as mechanical allodynia (C; measured in grams). *p<0.05, p<0.01 and *p<0.001 vs. vehicle; ###p<0.001 vs. sham-operated mice.

Example 12: Analgesic Activity on Inflammatory Pain

Formalin is injected into the plantar surface of the left hind paw and the response is the amount of time the animals spend licking the injected paw. Two distinct periods of high licking activity can be identified, an early phase lasting the first 5 min and a late phase lasting from 10 to 50 min after the injection of formalin. Nocifensive behavior is monitored (licking and biting of the injected paw) for 45 min in blocks of 5 min each.

NAI-112a/b is injected intraperitoneally at 1, 3 and 10 mg/kg, 30 min before formalin injection. As shown in FIG. 16, the highest doses of 3 and 10 mg/kg are able to reduce both first and second phase. FIG. 16 shows anti-inflammatory effects of NAI-112a/b in the formalin model in mice. NAI-112a/b (1-10 mg/kg, intraperitoneally) reduces time spent in licking and biting the inflamed paw (measured in seconds). *$p<0.05$ and **$p<0.01$ vs. vehicle-treated mice.

The invention claimed is:
1. A peptide compound having general formula (I)

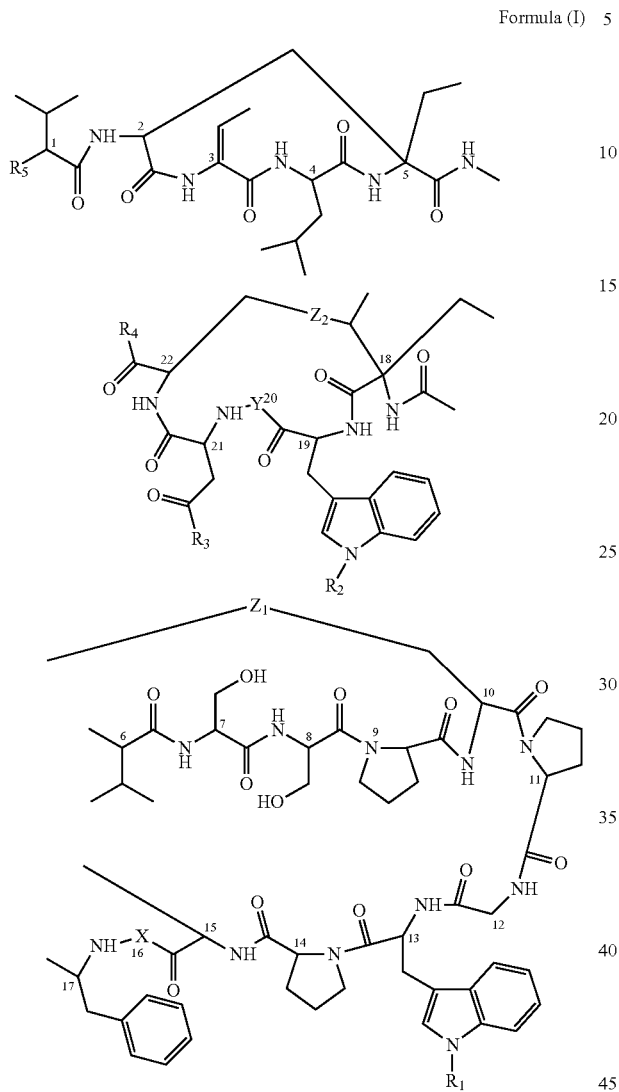

Formula (I)

$R_1$ and $R_2$ are independently selected among H or a sugar moiety chosen among monosaccharides, disaccharides, trisaccharides, oligosaccharides and their corresponding deoxy derivatives;

$R_3$ and $R_4$ are independently selected among OH, $NH_2$, $NR_6R_7$ wherein $R_6$ and $R_7$ independently represent:
  hydrogen; or
  an alkyl of 1 to 20 carbon atoms wherein said alkyl being linear, branched, cyclic or combinations thereof; or
  an alkenyl of 2 to 20 carbon atoms wherein said alkenyl being linear, branched, cyclic or combinations thereof; or
  an alkynyl of 2 to 20 carbon atoms wherein said alkynyl being linear, branched, cyclic or combinations thereof; or
  a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a benzyl radical optionally substituted on the phenyl ring by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a naphthyl radical optionally substituted by one or two substituents selected from halo, lower alkyl of 1 to 4 carbon atoms optionally substituted by 1 to 3 halogen atoms, and lower alkoxy of 1 to 4 carbon atoms optionally substituted by 1 to 3 halogen atoms; or a group of formula

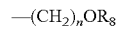
  —$(CH_2)_nOR_8$ in which n represents an integer from 2 to 8 and $R_8$ represents
  hydrogen; or
  $(C_1$-$C_4)$ alkyl; or
  a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a group of formula —(CH$_2$)$_n$NR$_9$R$_{10}$ in which n represents an integer from 2 to 8 and R$_9$ and R$_{10}$ independently represent hydrogen; or (C$_1$-C$_4$) alkyl; or a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a benzyl radical optionally substituted on the phenyl ring by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms;

R$_9$ and R$_{10}$ taken together represent a —(CH$_2$)$_3$, —(CH$_2$)$_4$—, —(CH$_2$)$_2$—O—(CH$_2$)$_2$, —(CH$_2$)$_2$—S—(CH$_2$)$_2$; or R$_9$ and R$_{10}$ taken together with the adjacent nitrogen atom represent: a piperazine moiety which may be substituted in position 4 with a substituent selected from (C$_1$-C$_4$) alkyl, (C$_3$-C$_8$) cycloalkyl, pyridyl, benzyl and substituted benzyl wherein the phenyl moiety bears 1 or 2 substituents selected from chloro, bromo, nitro, (C$_1$-C$_4$) alkyl and (C$_1$-C$_4$) alkoxy;

R$_5$ is selected as NR$_{11}$R$_{12}$ wherein R$_{11}$ and R$_{12}$ independently represent:

hydrogen; or an alkyl of 1 to 20 carbon atoms wherein said alkyl being linear, branched, cyclic or combinations thereof; or an alkenyl of 2 to 20 carbon atoms wherein said alkenyl being linear, branched, cyclic or combinations thereof; or an alkynyl of 2 to 20 carbon atoms wherein said alkynyl being linear, branched, cyclic or combinations thereof; or a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a benzyl radical optionally substituted on the phenyl ring by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a naphthyl radical optionally substituted by one or two substituents selected from halo, lower alkyl of 1 to 4 carbon atoms optionally substituted by 1 to 3 halogen atoms, and lower alkoxy of 1 to 4 carbon atoms optionally substituted by 1 to 3 halogen atoms; or a group of formula —$(CH_2)_nOR_8$ in which n represents an integer from 2 to 8 and $R_8$ represent hydrogen; or $(C_1-C_4)$ alkyl; or a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a group of formula —$(CH_2)_nNR_9R_{10}$ in which n represents an integer from 2 to 8 and $R_9$ and $R_{10}$ independently represent hydrogen; or $(C_1-C_4)$ alkyl; or a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a benzyl radical optionally substituted on the phenyl ring by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms;

$R_9$ and $R_{10}$ taken together represent a —$(CH_2)_3$, —$(CH_2)_4$—, —$(CH_2)_2$—O—$(CH_2)_2$, —$(CH_2)_2$—S—$(CH_2)_2$; or $R_9$ and $R_{10}$ taken together with the adjacent nitrogen atom represent: a piperazine moiety which may be substituted in position 4 with a substituent selected from $(C_1-C_4)$ alkyl, $(C_3-C_8)$ cycloalkyl, pyridyl, benzyl and substituted benzyl wherein the phenyl moiety bears 1 or 2 substituents selected from chloro, bromo, nitro, $(C_1-C_4)$ alkyl and $(C_1-C_4)$ alkoxy;

when $R_{11}$ or $R_{12}$ is hydrogen, $R_{12}$ or $R_{11}$ is —CO—$R_{13}$ where $R_{13}$ is selected among $NH_2$, or an alkyl of 1 to 20 carbon atoms wherein said alkyl being linear, branched, cyclic or combinations thereof; or an alkenyl of 2 to 20 carbon atoms wherein said alkenyl being linear, branched, cyclic or combinations thereof; or an alkynyl of 2 to 20 carbon atoms wherein said alkynyl being linear, branched, cyclic or combinations thereof; or a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a benzyl radical optionally substituted on the phenyl ring by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a naphthyl radical optionally substituted by one or two substituents selected from halo, lower alkyl of 1 to 4 carbon atoms optionally substituted by 1 to 3 halogen atoms, and lower alkoxy of 1 to 4 carbon atoms optionally substituted by 1 to 3 halogen atoms; or a group of formula —$(CH_2)_n OR_8$ in which n represents an integer from 2 to 8; and $R_8$ represents hydrogen; or $(C_1$-$C_4)$ alkyl; or a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a group of formula —$(CH_2)_n NR_9 R_{10}$ in which n represents an integer from 2 to 8; and $R_9$ and $R_{10}$ independently represent hydrogen; or $(C_1$-$C_4)$ alkyl; or a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a benzyl radical optionally substituted on the phenyl ring by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms;

$R_9$ and $R_{10}$ taken together represent a —$(CH_2)_3$, —$(CH_2)_4$—, —$(CH_2)_2$—O—$(CH_2)_2$, —$(CH_2)_2$—S—$(CH_2)_2$; or $R_9$ and $R_{10}$ taken together with the adjacent nitrogen atom represent: a piperazine moiety which may be substituted in position 4 with a substituent selected from $(C_1$-$C_4)$ alkyl, $(C_3$-$C_8)$ cycloalkyl, pyridyl, benzyl and substituted benzyl wherein the phenyl moiety bears 1 or 2 substituents selected from chloro, bromo, nitro, $(C_1$-$C_4)$ alkyl and $(C_1$-$C_4)$ alkoxy;

X and Y each independently represents an amino acid respectively in positions 16 and 20 of the peptide chain, wherein the amino acid is independently selected between Dha (dehydroalanine) and Ser (Serine);

$Z_1$ and $Z_2$ are independently chosen between the groups S, S—O—, S=O, O—S=O, and O=S=O, provided that when
$R_3$ and $R_4$ are both OH, or one of $R_3$ and $R_4$ is OH and the other is $NH_2$
then
$R_{11}$ and $R_{12}$ are not both hydrogen.

2. The peptide compound according to claim 1, wherein said deoxy derivatives are 6-deoxy derivatives.

3. The peptide compound according to claim 1, wherein said sugar moiety has the following formula (II):

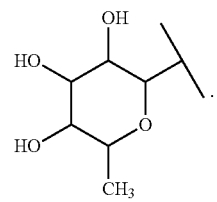

Formula (II)

4. The peptide compound according to claim 1, wherein in the position 16 of the peptide chain there is a Dha residue, while in the position 20 of the peptide chain there is a Ser residue.

5. The peptide compound according to claim 1, wherein in the position 16 of the peptide chain there is a Ser residue, while in the position 20 of the peptide chain there is a Dha residue.

6. The peptide compound according to claim 1, wherein said $Z_1$ and $Z_2$ are independently chosen as S.

7. A process for the preparation of peptide compounds according to claim 1, comprising culturing *Actinoplanes* sp. DSM 24059, recovering the compounds of formula (I) from the mycelium and/or from the fermentation broth and isolating the pure substance by chromatographic means, said process comprising a further step wherein compounds of formula (I) are chemically modified by semi-synthesis and/or converted into a physiologically tolerated salt.

8. A method of treatment of a disease or disorder in a mammal comprising the administration of an effective amount of a peptide compound having general formula (I)

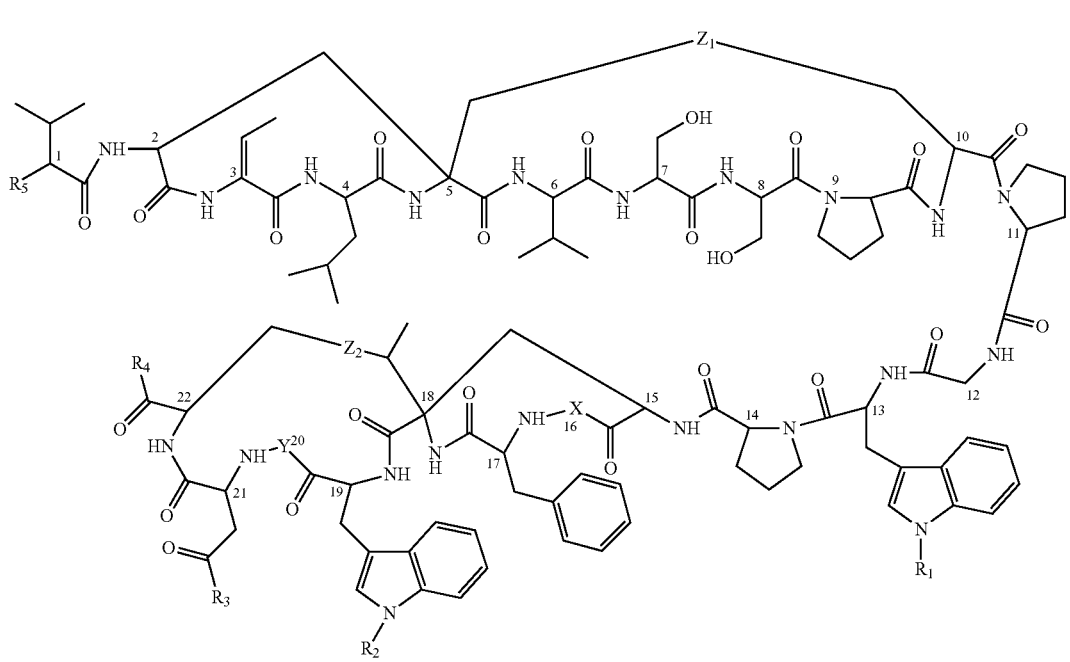

Formula (I)

wherein
$R_1$ and $R_2$ are independently selected among H or a sugar moiety chosen among monosaccharides, disaccharides, trisaccharides, oligosaccharides and their corresponding deoxy derivatives;

$R_3$ and $R_4$ are independently selected among OH, $NH_2$, $NR_6R_7$ wherein $R_6$ and $R_7$ independently represent:
hydrogen; or
an alkyl of 1 to 20 carbon atoms wherein said alkyl being linear, branched, cyclic or combinations thereof; or
an alkenyl of 2 to 20 carbon atoms wherein said alkenyl being linear, branched, cyclic or combinations thereof; or
an alkynyl of 2 to 20 carbon atoms wherein said alkynyl being linear, branched, cyclic or combinations thereof); or
a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or
a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or
a benzyl radical optionally substituted on the phenyl ring by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or
a naphthyl radical optionally substituted by one or two substituents selected from halo, lower alkyl of 1 to 4 carbon atoms optionally substituted by 1 to 3 halogen atoms, and lower alkoxy of 1 to 4 carbon atoms optionally substituted by 1 to 3 halogen atoms; or
a group of formula $$-(CH_2)_nOR_8$$

in which n represents an integer from 2 to 8 and $R_8$ represents
hydrogen; or
$(C_1-C_4)$ alkyl; or
a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or
a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or
a group of formula $$-(CH_2)_nNR_9R_{10}$$

in which n represents an integer from 2 to 8 and $R_9$ and $R_{10}$ independently represent
hydrogen; or
$(C_1-C_4)$ alkyl; or
a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or
a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a benzyl radical optionally substituted on the phenyl ring by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms;

$R_9$ and $R_{10}$ taken together represent a —$(CH_2)_3$—, —$(CH_2)_4$—, —$(CH_2)_2$—O—$(CH_2)_2$—, —$(CH_2)_2$—S—$(CH_2)_2$—; or $R_9$ and $R_{10}$ taken together with the adjacent nitrogen atom represent: a piperazine moiety which may be substituted in position 4 with a substituent selected from ($C_1$-$C_4$) alkyl, ($C_3$-$C_8$) cycloalkyl, pyridyl, benzyl and substituted benzyl wherein the phenyl moiety bears 1 or 2 substituents selected from chloro, bromo, nitro, ($C_1$-$C_4$) alkyl and ($C_1$-$C_4$) alkoxy;

$R_5$ is selected as $NR_{11}R_{12}$ wherein $R_{11}$ and $R_{12}$ independently represent:

hydrogen; or an alkyl of 1 to 20 carbon atoms wherein said alkyl being linear, branched, cyclic or combinations thereof; or an alkenyl of 2 to 20 carbon atoms wherein said alkenyl being linear, branched, cyclic or combinations thereof; or an alkynyl of 2 to 20 carbon atoms wherein said alkynyl being linear, branched, cyclic or combinations thereof; or a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a benzyl radical optionally substituted on the phenyl ring by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a naphthyl radical optionally substituted by one or two substituents selected from halo, lower alkyl of 1 to 4 carbon atoms optionally substituted by 1 to 3 halogen atoms, and lower alkoxy of 1 to 4 carbon atoms optionally substituted by 1 to 3 halogen atoms; or a group of formula —$(CH_2)_nOR_8$ in which n represents an integer from 2 to 8 and $R_8$ represent hydrogen; or ($C_1$-$C_4$) alkyl; or a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a group of formula

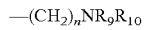

in which n represents an integer from 2 to 8 and $R_9$ and $R_{10}$ independently represent hydrogen; or $(C_1-C_4)$ alkyl; or a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a benzyl radical optionally substituted on the phenyl ring by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms;

$R_9$ and $R_{10}$ taken together represent a $-(CH_2)_3-$, $-(CH_2)_4-$, $-(CH_2)_2-O-(CH_2)_2$, $-(CH_2)_2-S-(CH_2)_2$; or $R_9$ and $R_{10}$ taken together with the adjacent nitrogen atom represent: a piperazine moiety which may be substituted in position 4 with a substituent selected from $(C_1-C_4)$ alkyl, $(C_3-C_8)$ cycloalkyl, pyridyl, benzyl and substituted benzyl wherein the phenyl moiety bears 1 or 2 substituents selected from chloro, bromo, nitro, $(C_1-C_4)$ alkyl and $(C_1-C_4)$ alkoxy;

when $R_{11}$ or $R_{12}$ is hydrogen, $R_{12}$ or $R_{11}$ is $-CO-R_{13}$ where $R_{13}$ is selected among $NH_2$, or an alkyl of 1 to 20 carbon atoms wherein said alkyl being linear, branched, cyclic or combinations thereof; or an alkenyl of 2 to 20 carbon atoms wherein said alkenyl being linear, branched, cyclic or combinations thereof; or an alkynyl of 2 to 20 carbon atoms wherein said alkynyl being linear, branched, cyclic or combinations thereof; or a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a benzyl radical optionally substituted on the phenyl ring by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a naphthyl radical optionally substituted by one or two substituents selected from halo, lower alkyl of 1 to 4 carbon atoms optionally substituted by 1 to 3 halogen atoms, and lower alkoxy of 1 to 4 carbon atoms optionally substituted by 1 to 3 halogen atoms; or a group of formula

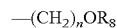

in which n represents an integer from 2 to 8; and $R_8$ represents hydrogen; or ($C_1$-$C_4$) alkyl; or a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a group of formula —(CH$_2$)$_n$NR$_9$R$_{10}$ in which n represents an integer from 2 to 8; and $R_9$ and $R_{10}$ independently represent hydrogen; or ($C_1$-$C_4$) alkyl; or a cycloalkyl of 3 to 8 carbon atom optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a phenyl radical optionally substituted by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms; or a benzyl radical optionally substituted on the phenyl ring by one or two substituents independently selected from halo, cyano, lower alkyl of 1 to 4 carbon atoms optionally substituted by 1 to 3 halogen atoms, lower alkoxy of 1 to 4 carbon atoms optionally substituted by 1 to 3 halogen atoms, phenyl, phenyl-lower alkyl of 1 to 4 carbon atoms, phenoxy, phenoxy-lower alkyl of 1 to 4 carbon atoms wherein the phenyl and the phenyl portion of the phenyl lower-alkyl, phenoxy and phenoxy-lower alkyl group is optionally substituted by one or two substituents selected from halo, cyano, lower alkyl of 1 to 4 carbon atoms optionally substituted by 1 to 3 halogen atoms, and lower alkoxy of 1 to 4 carbon atoms optionally substituted by 1 to 3 halogen atoms;

$R_9$ and $R_{10}$ taken together represent a —(CH$_2$)$_3$, —(CH$_2$)$_4$—, —(CH$_2$)$_2$—O—(CH$_2$)$_2$, —(CH$_2$)$_2$—S—(CH$_2$)$_2$; or $R_9$ and $R_{10}$ taken together with the adjacent nitrogen atom represent: a piperazine moiety which may be substituted in position 4 with a substituent selected from ($C_1$-$C_4$) alkyl, ($C_3$-$C_8$) cycloalkyl, pyridyl, benzyl and substituted benzyl wherein the phenyl moiety bears 1 or 2 substituents selected from chloro, bromo, nitro, ($C_1$-$C_4$) alkyl and ($C_1$-$C_4$) alkoxy;

X and Y each independently represents an amino acid respectively in positions 16 and 20 of the peptide chain, wherein the amino acid is independently selected between Dha (dehydroalanine) and Ser (Serine);

$Z_1$ and $Z_2$ are independently chosen between the groups S, S—O—, S=O, O—S=O, and O=S=O;

wherein the disease or disorder is selected from the group consisting of pain;

inflammatory pain;

neuropathic pain;

cancer pain;

pain induced by chemotherapy treatment;

migraine;

topical anaesthesia; and general anaesthesia.

9. The method according to claim 8, wherein said disease or disorder is selected from the group consisting of pain inflammatory pain, neuropathic pain, cancer pain and pain induced by chemotherapy treatment.

10. The method according to claim 9, wherein said disease or disorder is chronic neuropathic pain.

11. The method of claim 8 wherein said X in position 16 is Dha, said Y in position 20 is Ser, said $Z_1$ and $Z_2$ are S, said $R_1$ is 6-deoxy hexose of formula (II)

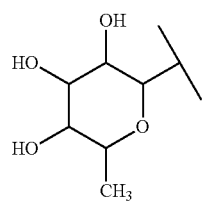

Formula (II)

and said $R_2$ is H, said $R_4$ is OH and said $R_3$ is $NH_2$, said $R_5$ is $NR_{11}R_{12}$ where $R_{11}$ and $R_{12}$ are H.

12. The method of claim 8 wherein said X in position 16 is Ser, said Y in position 20 is Dha, said $Z_1$ and $Z_2$ are S, said $R_1$ is 6-deoxy hexose of formula (II)

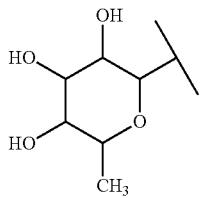

Formula (II)

and said $R_2$ is H, said $R_4$ is OH and said $R_3$ is $NH_2$ said $R_5$ is $NR_{11}R_{12}$ where $R_{11}$ and $R_{12}$ are H.

13. The method of claim 8 wherein said X in position 16 is Dha, said Y in position 20 is Ser, said $Z_1$ and $Z_2$ are S, said $R_1$ is 6-deoxy hexose of formula (II)

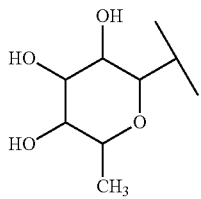

Formula (II)

and said $R_2$ is H, said $R_4$ and said $R_3$ are OH, said $R_5$ is $NR_{11}R_{12}$ where $R_{11}$ and $R_{12}$ are H.

14. The method of claim 8 wherein said X in position 16 is Ser, said Y in position 20 is Dha, said $Z_1$ and $Z_2$ are S, said $R_1$ is 6-deoxy hexose of formula (II)

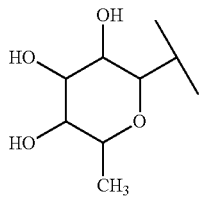

Formula (II)

and said $R_2$ is H, said $R_4$ and said $R_3$ are OH, said $R_5$ is $NR_{11}R_{12}$ where $R_{11}$ and $R_{12}$ are H.

15. Pharmaceutical compositions comprising at least a peptide compound according to claim 1 as active ingredient in addition to conventional excipients.

16. Method of treatment of a disease or disorder in a mammal comprising the administration of an effective amount of pharmaceutical compositions comprising the peptide compound according to claim 8 as the active ingredient in addition to conventional excipients; wherein the disease or disorder is selected from the group consisting of pain;
inflammatory pain;
neuropathic pain;
cancer pain;
pain induced by chemotherapy treatment;
migraine;
topical anaesthesia; and
general anaesthesia.

17. The method according to claim 16, wherein said disease or disorder is selected from the group consisting of pain, inflammatory pain, neuropathic pain, cancer pain and pain induced by chemotherapy treatment.

18. The method according to claim 17, wherein said neuropathic pain is chronic neuropathic pain.

\* \* \* \* \*